(12) United States Patent
Thompson et al.

(10) Patent No.: US 11,965,851 B2
(45) Date of Patent: Apr. 23, 2024

(54) GRID COATINGS FOR CAPTURE OF PROTEINS AND OTHER COMPOUNDS

(71) Applicant: Purdue Research Foundation, West Lafayette, IN (US)

(72) Inventors: David H. Thompson, West Lafayette, IN (US); Christopher Benjamin, Sunnyvale, CA (US); Kyle Wright, Lafayette, IN (US); Scott C. Bolton, West Lafayette, IN (US); Seok-Hee Hyun, West Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 209 days.

(21) Appl. No.: 17/075,793

(22) Filed: Oct. 21, 2020

(65) Prior Publication Data

US 2021/0041388 A1    Feb. 11, 2021

Related U.S. Application Data

(62) Division of application No. 16/063,029, filed as application No. PCT/US2016/067391 on Dec. 16, 2016, now Pat. No. 10,989,681.

(60) Provisional application No. 62/380,586, filed on Aug. 29, 2016, provisional application No. 62/268,737, filed on Dec. 17, 2015.

(51) Int. Cl.
| | |
|---|---|
| *G01N 27/12* | (2006.01) |
| *C01B 32/192* | (2017.01) |
| *G01N 1/30* | (2006.01) |
| *G01N 27/414* | (2006.01) |
| *H01J 37/20* | (2006.01) |
| *B82Y 30/00* | (2011.01) |
| *B82Y 40/00* | (2011.01) |
| *C07K 1/14* | (2006.01) |

(52) U.S. Cl.
CPC ......... *G01N 27/127* (2013.01); *C01B 32/192* (2017.08); *G01N 1/30* (2013.01); *G01N 27/4145* (2013.01); *H01J 37/20* (2013.01); *B82Y 30/00* (2013.01); *B82Y 40/00* (2013.01); *C07K 1/14* (2013.01); *G01N 2223/418* (2013.01)

(58) Field of Classification Search
CPC ....... B82Y 30/00; B82Y 40/00; C01B 32/192; C07K 1/14; G01N 1/30; G01N 2223/418; G01N 27/127; G01N 27/4145; H01J 37/20
See application file for complete search history.

(56) References Cited

U.S. PATENT DOCUMENTS

| | | |
|---|---|---|
| 8,629,076 B2 | 1/2014 | Worsley et al. |
| 8,803,629 B2 | 8/2014 | Shirakawa et al. |
| 10,989,681 B2 * | 4/2021 | Thompson ............... H01J 37/20 |
| 2014/0154770 A1 * | 6/2014 | Vittadello .............. B82Y 30/00 |
| | | 435/177 |
| 2019/0003999 A1 | 1/2019 | Thompson et al. |

FOREIGN PATENT DOCUMENTS

| | | |
|---|---|---|
| CN | 201210111322 A | 9/2012 |
| WO | 2009154688 A1 | 12/2009 |
| WO | 2012094634 A2 | 7/2012 |
| WO | 2013019729 A1 | 2/2013 |
| WO | 2017106797 A1 | 6/2017 |
| WO | 2020041202 A1 | 2/2020 |

OTHER PUBLICATIONS

Ali et al., "Lipid-Lipid Interactions in Aminated Reduced Graphene Oxide Interface for Biosensing Application," Langmuir, 2014, vol. 30, No. 14, pp. 4192-4201.*
Zhang et al., "Functionalized graphene oxide for the fabrication of paraoxon biosensors," Anal. Chim. Acta, 2014, vol. 827, pp. 86-94.*
Kelly D. et al., The Affinity Grid: A Pre-fabricated EM Grid for Monolayer Purification. Journal of molecular biology 382, 423-433, 2008.
Kelly D. et al., Monolayer purification: a rapid method for isolating protein complexes for single-particle electron microscopy. Proceedings of the National Academy of Sciences of the United States of America 105, 4703-4708, 2008.
Kelly D. et al., Strategy for the use of affinity grids to prepare non-His-tagged macromolecular complexes for single-particle electron microscopy. Journal of Molecular Biology 400, 675-681, 2010.
Thompson, D. et al., Design, synthesis, and performance of NTA-modified lipids as templates for histidine-tagged protein crystallization. Chemistry Letters 36, 956-975, 2007.
Barklis, E., et al.,Structural analysis of membrane-bound retrovirus capsid proteins, The EMBO Journal 16, 1199-1213, 1997.
Benjamin, C. W., et al., Non-fouling NTA-PEG-based TEM Grid Coatings for Selective Capture of Histidine-tagged Protein Targets from Cell Lysates, Langmuir 2016, 32, 551-559.
Jiang, H.-L. et al., From Metal-Organic Framework to Nanoporous carbon: Toward a very high surface area ond hydrogen uptake, JACS, 2011, 133, 11854-11857.
Liu, Z. et al., A Graphene Oxide.Streptavidin Complex for Biorecognition—Towards affinity purification, Adv. Funct. Mater., 2010, 20, 2857-2865.
Palovcak, E. et al., A simple robust procedure for preparing graphene-oxide cryo-EM grids, Journal of Structural Biology, 2018, 204, 80-84.
Pantelic, R. S., et al., Graphene oxide: A substrate for optimizing preparations of frozen-hydrated samples, Journal of Structural Biology, 2010, 170, 152-156.

(Continued)

*Primary Examiner* — Galina M. Yakovleva
(74) *Attorney, Agent, or Firm* — Reichel Stohry Dean LLP; Natalie J. Dean

(57) ABSTRACT

Methods of using grids in connection with suitable microscopy techniques, such as for determining the structure of target compounds including proteins, are disclosed. Said grid comprising a coating modified with one or more capture agents and a deactivating agent.

8 Claims, 8 Drawing Sheets

Specification includes a Sequence Listing.

(56) References Cited

OTHER PUBLICATIONS

Liu N., et al., Bioactive functionalized monolayer graphene for high-resolution cryo-electron microscopy, JACS, 2019, 141, 4016-4025.
Naydenova, K. et al., Multifunctional graphene supports for electron cryomicroscopy, PNAS, 2019, 116, No. 24, 11718-11724.
Benjamin, C. W., et al., Selective Capture of Histidine-tagged Proteins from Cell Lysates Using TEM grids Modified with NTA-Graphene Oxide, Scientific Reports, 2016, 6:32500, DOI: 10.1038/srep32500.
USPTO, Notice of Allowance for U.S. Appl. No. 16/063,029 (Publication No. US20190003999A1), dated Oct. 1, 2020, 20 pages.
Thompson, et al., Response under 37 CFR 1.111 to the Office Action dated Apr. 17, 2020 for the U.S. Appl. No. 16/063,029 (Publication No. US20190003999A1), dated Jul. 17, 2020, 13 pages.
USPTO, Non Final Office Action for U.S. Appl. No. 16/063,029 (Publication No. US20190003999A1), dated Apr. 17, 2020, 22 pages.
ISA/US, International Search Report for PCT international patent application serial No. PCTUS1667391, dated Mar. 24, 2017, 4 pages.
ISA/US, Written Opinion of the International Searching Authority for PCT international patent application serial No. PCTUS1667391, dated Mar. 24, 2017, 6 pages.
ISA/US, International Preliminary Report on Patentability for PCT international patent application serial No. PCTUS1667391, dated Jun. 19, 2018, 7 pages.

\* cited by examiner

```
                         SEQUENCE LISTING

<160> NUMBER OF SEQ ID NOS: 6

<210> SEQ ID NO 1
<211> LENGTH: 9
<212> TYPE: PRT
<213> ORGANISM: Artificial Sequence
<220> FEATURE:
<223> OTHER INFORMATION: Synthesized

<400> SEQUENCE: 1

Tyr Pro Tyr Asp Val Pro Asp Tyr Ala
1               5

<210> SEQ ID NO 2
<211> LENGTH: 9
<212> TYPE: PRT
<213> ORGANISM: Artificial Sequence
<220> FEATURE:
<223> OTHER INFORMATION: Synthesized

<400> SEQUENCE: 2

Glu Gln Lys Leu Ile Ser Glu Glu Asp
1               5

<210> SEQ ID NO 3
<211> LENGTH: 8
<212> TYPE: PRT
<213> ORGANISM: Artificial Sequence
<220> FEATURE:
<223> OTHER INFORMATION: Synthesized

<400> SEQUENCE: 3
```

```
Asp Tyr Lys Asp Asp Asp Asp Lys
1               5

<210> SEQ ID NO 4
<211> LENGTH: 14
<212> TYPE: PRT
<213> ORGANISM: Artificial Sequence
<220> FEATURE:
<223> OTHER INFORMATION: Synthesized

<400> SEQUENCE: 4

Gly Lys Pro Ile Pro Asn Pro Leu Leu Gly Leu Asp Ser Thr
1               5                   10

<210> SEQ ID NO 5
<211> LENGTH: 17
<212> TYPE: PRT
<213> ORGANISM: Artificial Sequence
<220> FEATURE:
<223> OTHER INFORMATION: Synthesized

<400> SEQUENCE: 5

Met Arg Gly Ser His His His His His His Thr Asp Pro Ala Leu Arg
1               5                   10                  15

Ala

<210> SEQ ID NO 6
<211> LENGTH: 5
<212> TYPE: PRT
<213> ORGANISM: Artificial Sequence
<220> FEATURE:
<223> OTHER INFORMATION: Synthesized

<400> SEQUENCE: 6

Gly Leu Cys Gly Arg
1               5
```

GRID COATINGS FOR CAPTURE OF PROTEINS AND OTHER COMPOUNDS

CROSS-REFERENCE TO RELATED APPLICATIONS

The present application is a divisional of U.S. Nonprovisional patent application Ser. No. 16/063,029, filed on Jun. 15, 2018, which was a 35 U.S.C. § 371 National Phase Application of International Patent Application No. PCT/US2016/067391, filed on Dec. 16, 2016, which claims the benefit of U.S. Provisional Patent Application Ser. No. 62/268,737, filed on Dec. 17, 2015, and U.S. Provisional Patent Application Ser. No. 62/380,586, filed Aug. 29, 2016. The contents of each of the aforementioned applications are incorporated herein by reference in their entirety.

STATEMENT REGARDING GOVERNMENT FUNDING

This invention was made with government support under GM098017 awarded by the National Institute of Health. The government has certain rights in the invention.

BACKGROUND

Single particle cryo-electron microscopy analysis (SPA) is a rapidly growing method for elucidating structure of biological materials at near atomic resolution due to recent advances in instrumentation and computational algorithms. One aspect of the SPA process that is not well optimized, however, is sample preparation. Traditionally, proteins targeted for structural analysis must be overexpressed and subjected to time-consuming purification and concentration steps, sometimes under harsh conditions that disrupt protein-protein interactions of interest. Recently, there have been efforts reported that seek to address these limitations, either by improving grid rigidity to reduce beam-induced motion or by effecting on-grid purification with "affinity grids" that employ metal chelating lipids that were originally developed for two-dimensional protein crystallization at the lipid-water interface. The latter approach seeks to selectively capture biological target molecules from complex mixtures such as cell lysates as an integral part of the TEM sample preparation process.

In preparing biological samples for electron microscopy analysis, samples may be spread on an electron microscopy grid and preserved in a frozen-hydrated state by rapid freezing, often in liquid ethane near liquid nitrogen temperature. By maintaining specimens at liquid nitrogen temperature or colder, they can be introduced into the high-vacuum of the electron microscope column. Most biological specimens are extremely radiation sensitive, so they are imaged with low-dose techniques (usefully, the low temperature of cryo-electron microscopy provides an additional protective factor against radiation damage).

Consequently, the images tend to be very noisy. For some biological systems, it is possible to average images to increase the signal-to-noise ratio and retrieve high-resolution information about the specimen using the technique known as single particle analysis. This approach in general requires that the things being averaged are identical, although some limited conformational heterogeneity can now be studied (e.g., ribosomes).

To better address these limitations, there have been efforts to either improve grid rigidity to reduce beam-induced motion or effect on-grid purification with 'affinity grids" that employ metal chelating lipids that were originally developed for two-dimensional protein crystallization at the lipid-water interface. The latter approach seeks to selectively capture biological target molecules from complex mixtures such as cell lysates as an integral part of the TEM sample preparation process.

Although lipid monolayer affinity grids have shown some success in producing samples for cryo-EM reconstruction at 20 Å resolution, robust performance of the reported grid coatings is limited by film instability and non-uniformity under the evaporative casting methods that are often employed. Additionally, these lipid films require a thin polymer layer or a holey carbon substrate layer to provide mechanical support of the deposited film.

SUMMARY OF THE INVENTION

In one aspect of the disclosure, a grid comprising a coating modified with one or more capture agents and further comprising a deactivating agent is provided.

In a further aspect of the disclosure, a method for preparing targets for structure elucidation comprising contacting a grid comprising a coating modified with one or more capture agents and further comprising a deactivating agent with a cell lysate comprising proteins and subjecting the proteins to a suitable microscopy for structure analysis is provided.

DETAILED DESCRIPTION OF THE EXEMPLARY EMBODIMENTS

Figure 1:
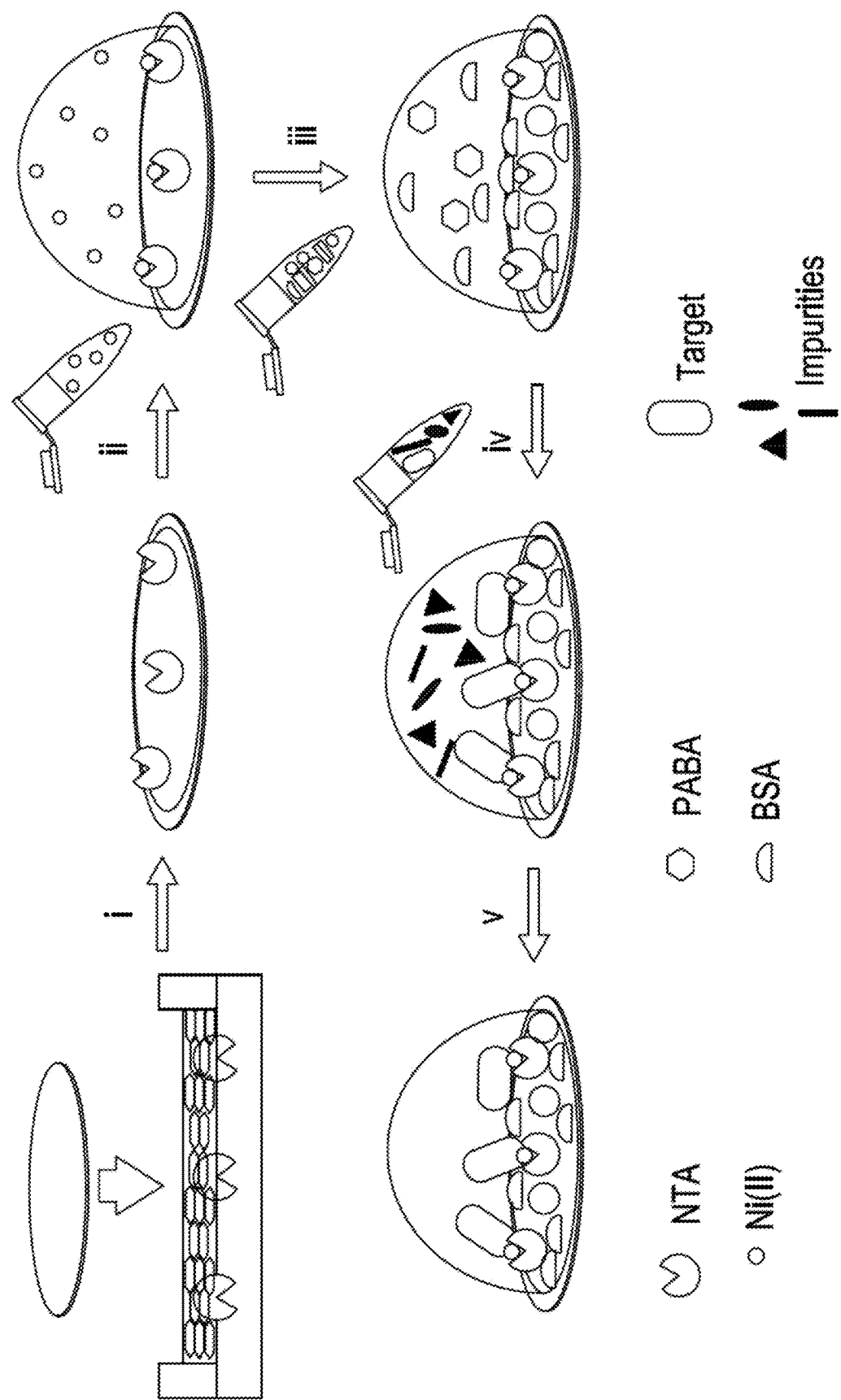
FIG. 1. A schematic illustrating sample preparation using a graphene oxide-nitrilotriacetic acid (GO-NTA) modified TEM grid.

While the concepts of the present disclosure are illustrated and described in detail in the figures and the description herein, results in the figures and their description are to be considered as exemplary and not restrictive in character; it being understood that only the illustrative embodiments are shown and described and that all changes and modifications that come within the spirit of the disclosure are desired to be protected. Unless defined otherwise, the scientific and technology nomenclatures have the same meaning as commonly understood by a person in the ordinary skill in the art pertaining to this disclosure.

Novel grids with desired elasticity and rigidity to perform single particle analysis using electron microscopy are herein disclosed. The grids operate by selectively capturing targets of interest for analysis while not capturing contaminants or other interferants. Grids comprising coatings modified with at least one capture agent that can specifically target desired compounds, such as proteins in a biological sample through affinity purification, and deactivating agents to block non-specific binding between the grid and non-target proteins in the same biological sample are provided. The grids herein disclosed are able to operate at higher resolutions than previous grids without the disadvantages in the prior art.

The grid surface components and the combination thereof enable the benefits of the disclosure. The grids contain a coating that is modified with one or more capture agents. This modification enables grids to interact with the target of interest via the one or more capture agents. The deactivating agent or agents are present to help prevent contaminants and interferents from adhering to the grids. Such grids may then be used in a screening assay, for example, to capture proteins containing a particular structure. For example, one may be interested in identifying the structure of proteins that bind to a particular antibody. In such embodiments, the capture agents may be a grid-immobilized antibody or antibody fragments that recognize corresponding antigens on the protein targets. Alternatively, the capture agents could be small-molecule drug candidates that have been attached to the grid coatings where the protein target would be captured via a high affinity drug-protein interaction. This would enable appropriate selection of the most promising drug candidate from a collection of compounds based on the site of engagement of the drug-protein interaction and on the heterogeneity of the proteins captured, such as cell lysates.

Examples of coatings to be modified with one or more capture agents include graphene, graphene oxide, microporous materials, nano-porous materials, metal-organic frameworks, activated carbon, microporous carbon, nanoporous carbon, organic membranes, aerogels such as carbon aerogel or a metal oxide aerogel, and zeolites. The coating may be an atomic film of an element with a "low" Z (atomic number) such as carbon. The coating may be deployed in various thicknesses such as between 0.1 nm and 100 µm, 0.1 nm and 100 nm thick, 0.1 nm and 10 nm thick, 0.1 nm and 2 nm thick, and 0.1 nm and 1 nm thick. In such embodiments, the coating may be a single monolayer.

In some embodiments, the coating to be modified with one or more capture agents is a carbon-based coating such as based on graphene. Specific examples include graphene and graphene oxide ("GO"). The properties of graphene and graphene oxide are useful for using grids for structure analysis. The electrical conductivity of monolayer graphene, for example, is six orders of magnitude higher than amorphous carbon, and although the level of conductivity in graphene decreases with the extent of oxidation, it has been shown to recover much of this conductivity upon reduction with $H_2$ plasma. Additionally, unlike unsupported lipid monolayers, the elasticity of graphene-based grids allows them to resist permanent deformation due to mechanical transfer techniques from the material-water interface and such grids possess superior mechanical strength and conductivity. By utilizing target specificity with respect to grids of the disclosure, such as graphene-based grids, improved stability and resistance to non-specific adsorption such that direct capture from cell lysates has been shown.

The grid can be tuned to capture various target compounds, including proteins, based on the affinity between the target compound and the capture agent. The modification of the coating with the one or more capture agents may be through the formation of a covalent or non-covalent chemical bond or by way of electrostatic forces such as those often found between antigens and antibodies. The concept of using capture agents to select for compounds such as proteins is known in the art. Examples of capture agents include NTA, tris(nitrilotriacetic acid), glutathione, peptides, aptamers, antibodies, antibody fragments, or any high-affinity small molecule ligand that has an affinity to the target, such as a protein. Other examples of capture agents include a protein having affinity for antibodies, Fc regions of proteins, Fab regions of proteins, or Protein A/G, nucleotides, oligonucleotides, polynucleotides, analogs of nucleotides, ATP, lectin, heparin, a carbohydrate, ubiquitin, SNAP tag, glucosaminoglycan, chitin, or amylase. Table 1 represents examples of several known affinity interactions between capture agents and their various associated targets on proteins. Any of these capture agents may be used in connection with the associated targets with grids of the disclosure for structure analysis or elucidation, for example.

TABLE 1

Affinities Between Capture Agents and Targets

| Capture Agent | Associated Target |
| --- | --- |
| Nickel(II) or Cobalt(II):Nitrilotriacetic acid | Polyhistidine fusion |
| Glutathione | Glutathione S-transferase fusion |
| Alkyne | Azide-containing target |
| Azide | Alkyne-containing target |
| Maleimide | Thiol or amine-containing target |
| Biotin | Avidin, Streptavidin, NeutrAvidin ® (a deglycosylated version of avidin), CaptAvidin ™ (a protein including a nitrate tyrosine in its biotin-binding site) |
| Avidin, Streptavidin, NeutrAvidin ® (a deglycosylated version of avidin), CaptAvidin ™ (a protein including a nitrate tyrosine in its biotin-binding site) | Biotin fusion or modification |

TABLE 1-continued

Affinities Between Capture Agents and Targets

| Capture Agent | Associated Target |
|---|---|
| Antibody | Antigen |
| Antibody fragment | Antigen |
| Protein A, G or L | Antibody |
| anti-HA antibody or fragment | HA (YPYDVPDYA (SEQ ID NO: #1)) fusion |
| anti-Myc antibody or fragment | c-Myc (EQKLISEED (SEQ ID NO: #2)) fusion |
| ANTI-FLAG ® (an antibody to FLAG ®) antibody or fragment | FLAG ® (a polypeptide protein tag having the sequence motif DYKDDDDK) (DYKDDDDK (SEQ ID NO: #3)) fusion |
| anti-V5 antibody or fragment | V5 (GKPIPNPLLGLDST (SEQ ID NO: #4)) fusion |
| Maltose | Maltose binding protein (MBP) fusion |
| Halo | HaloTag ® (a polypeptide tag derived from a bacterial haloalkane dehalogenase wherein the tag is composed of two covalently bound segments including a haloalkane dehalogenase and a synthetic ligand of choice; Promega Corporation) fusion |
| Dibenzocyclooctyne | Azide-containing target |
| N-Hydroxysuccinimide | Thiol or amine-containing target |
| Amine | Amine-reactive target |
| $Ni^{2+}$:NTA-poly(ethylene glycol 2000)-1,2-distearoyl-sn-3-glycerophosphoethanolamine | Polyhistidine fusion |

Common capture agents that are covalently bound to the coating are chelating agents such as polycarboxylic acids. Specific capture agents include ethylenediaminetetraacetic acid (EDTA), diethylenetriaminepentaacetic acid (DTPA), diaminocyclohexanetetraacetic acid (DCTA), nitrilotris(methylene)triphosphonic acid (NTTA), 2-aminoethanethiol, thiobis(ethylenenitrilo)tetraacetic acid (TEDTA), N-2-acetamidoimino-diacetic acid (ADA), iminodiacetic acid (IDA), hydroxamic acid, carboxymethylated aspartate (CMA) and nitrilotriacetic acid (NTA), tris(nitrilotriacetic acid), $N^1,N^4,N^8$-tris(nitrilotriacetic acid)-1,4,8,11-tetraazocyclotetradecane and analogs or homologs thereof. When performing as capture agents in grids of the disclosure, the chelating agents are typically chelated to a metal ion. Examples of such ions include $Cu^{2+}$, $Ni^{2+}$, $Co^{2+}$, $Ca^{2+}$, $Mg^{2+}$, $Cd^{2+}$, $Gd^{2+}$, $Ru^{2+}$, and $Fe^{2+}$.

Table 2 illustrates certain capture agent-coating modifications, the nature of the interaction with the target protein of interest, the affinity tag used for the protein, the pH at which the chemistry operates and some relevant application.

TABLE 2

| Non-covalent Capture Method | Capture Agent | Specificity | Working pH | Applications |
|---|---|---|---|---|
| IMAC | NTA, Ni2+-activated (can be activated with other metal ions) | Histidine tag | 2-14 | Recombinant Histidine-tagged proteins |
| GST | Glutathione | GST tag | 1-14 | Recombinant GST-tagged Proteins |
| Protein A | Protein A | IgG | 2-10 | IgG-mediated capture of target protein |

TABLE 2-continued

| Non-covalent Capture Method | Capture Agent | Specificity | Working pH | Applications |
|---|---|---|---|---|
| Biotin | Streptavidin | Biotin | 4-10 | Biotinylated protein |

Table 3 is similar to Table 2 except it illustrates certain covalent capture agent-coating interactions.

TABLE 3

| Covalent Capture Method | Capture Agent | Specificity | Working pH | Applications |
|---|---|---|---|---|
| NHS | Amidation | Lysine | 3-11 | Capture at surface-exposed lysine residues |
| Maleimide | Thioether | Cysteine | 4-10 | Capture at surface-exposed cysteine residues |
| Cyclooctyne | "Click" reaction | Azide | 4-10 | Azidated protein |
| Boronate | Boronate ester | cis-diols | 2-10 | Capture of any target molecule containing a cis-1,2-diol |
| Amine | Amidation (after EDCI activation) | Aspartate, Glutamate | 2-10 | Capture at surface-exposed carboxylates |

Grids of the disclosure further comprise deactivating agents. Such deactivating agents defoul the surface of the grid to optimize analysis of the target by minimizing interference from other compounds and proteins. Without being bound by theory, it is believed that the deactivating agents tightly pack on the grid to remove binding locations for compounds or other proteins that are not captured by the capture agents. Thus, deactivating agents aid in the selectivity of the overall affinity of the grid and improve signal to noise by blocking non-specific target capture by the grid. Example of deactivating agents include, but are not limited to, water soluble polymers such as polyethylene glycols. Other examples include dextran, agarose, methoxy-poly (ethylene glycol 350)-1,2-distearoyl-sn-3-glycerophosphoethanolamine, albumin, bovine serum albumin, casein, or other protein, small molecule, or hydrophilic polymer that blocks non-specific absorption such as from proteins or other compounds.

In some embodiments, more than one deactivating agent may be used. For example, the deactivating agent 4-aminobenzoic acid (PABA) may be chemically bound to the chemically modified coating. In those embodiments, a second deactivating agent, such as BSA, may also be used which is not so chemically bound.

The targets of the disclosure may be one or more proteins or other compounds. For example, one may use the grids to capture organic molecules in a screen. A typical use, however, is to capture one or more target proteins of interest for structure analysis by electron microscopy. The proteins may or may not be tagged for such purposes. The proteins may be prepared in any number of conventional ways such as from a cell lysate-which may be clarified prior to capture with the grids of the disclosure. Cell lysates are often *E. coli*, plant, or human cell lysates. The capture agent is chosen so that it is selective for the interaction of interest between the capture agent and the target protein. It is known in the art to tag proteins with polyhistidine and compounds that are selective for polyhistidine include NTA. For example, poly histidine tags (or other peptide tags such as FLAG® (a polypeptide protein tag having the sequence motif DYKDDDDK (SEQ ID NO: 3)) or protein fusions such as Glutathione S-transferase) are typically engineered into an expression plasmid for the protein and transfected into *E. coli* such that the N- or C-terminus of the expressed protein bears the affinity tag. Thus, in some embodiments, the proteins of interest are tagged using known techniques in the art with polyhistidine wherein the grid comprises GO-NTA or GONTA-PABA as a coating. Other tags include Glutathione S-transferase, Avidin, Streptavidin, NeutrAvidin® (a deglycosylated version of avidin), CaptAvidin™ (a protein including a nitrated tyrosine in its biotin-binding site), biotin, an antigen, an antibody, HA (YPYDVPDYA (SEQ ID NO: 1)), c-Myc (EQKLISEED (SEQ ID NO: 2)), FLAG® ((apolypeptide protein tag having the sequence motif DYKDDDDK (SEQ ID NO: 3)), V5 (GKPIPNPLLGLDST (SEQ ID NO: 4)), Maltose binding protein, artificial amino acid modifications (e.g., alkyne or azide) or HaloTag® (a polypeptide tag derived from a bacterial haloalkane dehalogenase wherein the tag is composed of two covalently bound segments including a haloalkane dehalogenase and a synthetic ligand of choice; Promega Corporation). When so prepared, the protein target, immobilized on the surface as an ensemble of single particles with different orientations with respect to the surface normal, maybe imaged or otherwise analyzed with a suitable microscope such as an electron microscope or a Raman microscope. When the grid coating modified with the one or more capture agents is sufficiently thin, such as with a monolayer, the target may be presented in the same focal plane of the microscope, thus providing the advantage that both target and modified coating be in focus during image capture which is advantageous for obtaining high resolution structures.

Examples of resolutions obtained by the grids of the disclosure include resolutions to between 1 Å and 4 Å including between 2 Å and 4 Å and between 3 Å and 4 Å. In other embodiments, the resolution is between 1 Å and 10 Å including between 4 Å and 10 Å, 5 Å and 10 Å, 6 Å and 10 Å, 7 Å and 10 Å, 8 Å and 10 Å, and 8 Å and 9 Å and all values in between for these examples.

Structural analysis of proteins may be performed by contacting the grids of the disclosure with cell lysates comprising those proteins and then subjecting the proteins to a suitable microscopy, such as electron microscopy, including cryo-electron microscopy, transmission electron microscopy, or scanning electron microscopy. In some embodiments, the proteins are tagged with an affinity tag with example of such a tag being a polyhistidine tag. In some of these embodiments, a coating of graphene or GO may be modified with a chelating agent and a metal ion such as NTA and $Ni^{2+}$ and a PABA deactivating agent. The resolution obtained in these embodiments may be between 1 Å and 4 Å including between 2 Å and 4 Å and between 3 Å and 4 Å. In other embodiments, the resolution is between 1 Å and 10 Å including between 4 Å and 10 Å, 5 Å and 10 Å, 6 Å and 10 Å, 7 Å and 10 Å, 8 Å and 10 Å, and 8 Å and 9 Å and all values in between for these embodiments. When the grid is used in an electron microscope for analysis, it may be placed in a sample holder such as made out of a nonferrous metal.

In various embodiments of the disclosure, the coating comprises one or more graphene or GO sheets modified with one or more capture agents. When graphene or GO is modified with one or more capture agents, a commonly used capture agent, especially with polyhistidine tagged-proteins is $N\alpha$, $N\alpha$-dicarboxymethyllysine (which is the same as nitrilotriacetic acid and referred to herein as NTA).

In various embodiments, the coating may be modified with one or more lipid monolayers supported by a thin carbon or a graphene-type layer or by single wall carbon nanotubes. In these embodiments, depending on the structure of the monolayer, it may serve both as a capture agent and as a blocking agent. For example, a Ni-chelated NTA bound monolayer may act as a capture agent, even if bound to a polyethylene glycol group as in the case of $Ni^{2+}$:NTA-poly(ethylene glycol 2000)-1,2-distearoyl-sn-3-glycerophosphoethanolamine in Example 21. In that Example, methoxy-poly(ethylene glycol 350)-1,2-distearoyl-sn-3-glycerophosphoethanolamine acts as a deactivating agent.

In other embodiments, single wall carbon nanotubes are coated with a monolayer coating comprising a capture agent being one or more of NTA-PEG2000-DSPE or NTA-PEG-2000-DTPE and a deactivating agent such as mPEG350-DTPE.

In some embodiments, GO-modified grids are prepared, which have lower background signal and improved conductivity (which aids in combatting sample charging and instability during image capture) than previous lipid monolayer coated affinity grids. Such grids may be modified, for example, by covalently linking the grid coating to a chelating agent, such as $N^{\alpha}$, $N\alpha$-dicarboxymethyllysine to make GO-NTA. The GO-NTA may then be chelated to a metal ion such as $Cu^{2+}$, $Ni^{2+}$, $Co^{2+}$, $Ca^{2+}$, $Mg^{2+}$, $Cd^{2+}$, $Gd^{2+}$, $Ru^{2+}$, or $Fe^{2+}$. A common metal ion used is $Ni^{2+}$.

In one example, a GO-modified grid is shown in FIG. 1. In process step (i), a GO-NTA monolayer is deposed onto a transmission electron microscopy (TEM) grid via Langmuir-Schaefer (L-S) transfer. In step (ii), activation of NTA occurs with $Ni^{2+}$ (referred to as Ni(II) in FIG. 1) (or another divalent metal ion can be used). The blocking of non-specific reaction and/or adsorption sites with 4-aminobenzoic acid (PABA) and bovine serum albumin (BSA) occurs in step (iii). Incubation of clarified lysate containing the target with the blocked grid in step (iv), and the washing of non-target molecules (impurities) from the grid, followed by cryo-fixation or staining occurs in step (v). Using the general procedures illustrated in FIG. 1, both $His_6$-T7 bacteriophage and $His_6$-GroEL were selectively captured from cell lysates by a nickel-chelated single monolayer GO-NTA grid using bovine serum albumin (BSA) and PABA as deactivating agents. In the case of $His_6$-GroEL, multiple single particle analyses were performed on the protein with the highest resolution being at 8.1 Å.

EXAMPLES

Example 1. General Description of Functionalization of GO Sheets with NTA

Figure 2:
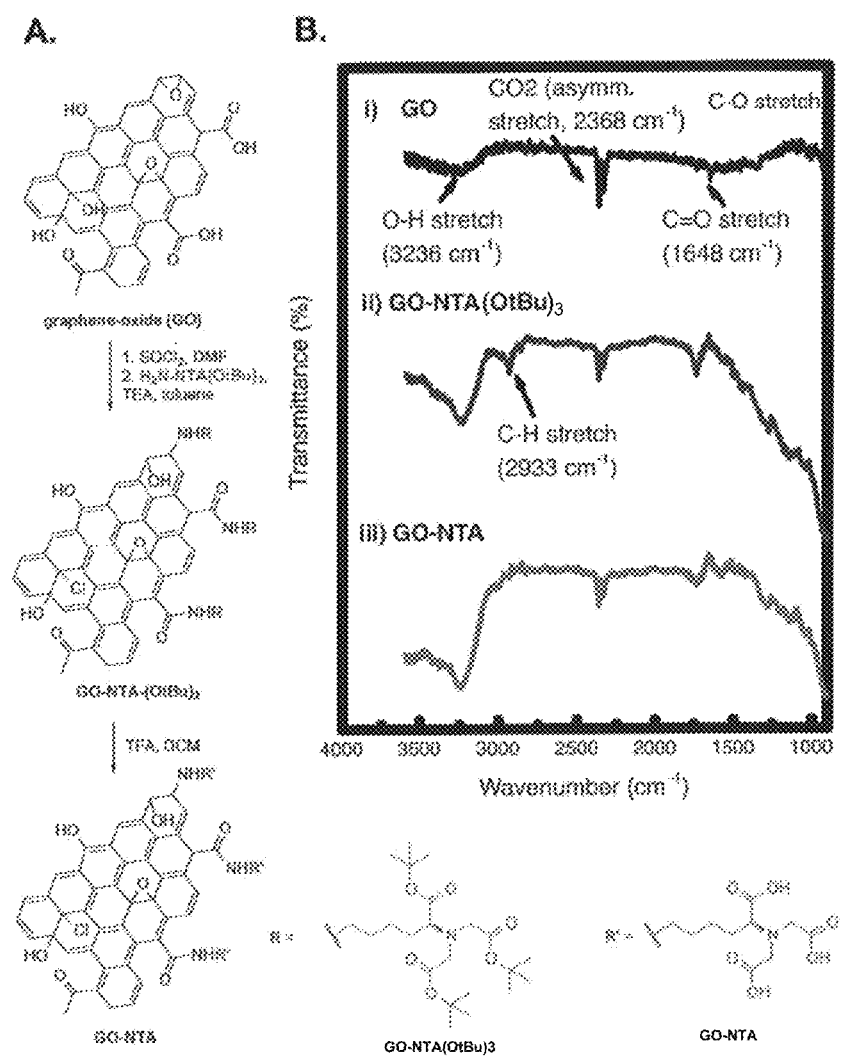
FIG. 2. (A) Reaction sequence for preparation of GO-NTA from GO; (B) Fourier transform infrared spectra of (i) GO, (ii) GO-NTA(O-t-Bu)3, and (iii) GO-NTA.

GO was produced from graphene using Hummer's method. Activation of the GO carboxylic acid groups with $SOCl_2$ prior to reaction with the tris-t-butyl ester of lysine NTA gave GO-NTA-(O-t-Bu)$_3$. TFA deprotection of this intermediate gave GO-NTA (FIG. 2A). Fourier transform infrared spectroscopy was used to monitor these reactions as shown in FIG. 2B. The spectra of GO displayed a broad absorption at 3236 cm$^{-1}$ (O—H stretch) and a sharper absorption at 1648 cm$^{-1}$ (C=O stretch). The NTA-GO tris-t-butyl ester displayed an additional absorption at 2933 cm$^{-1}$ (C—H stretch) due to the incorporation of the lysine and t-butyl moieties. Following treatment of NTA-GO tris-t-butyl ester with TFA, the presence of the aliphatic C—H stretching was greatly reduced, indicating successful deprotection of the NTA chelator substituents.

Figure 7:
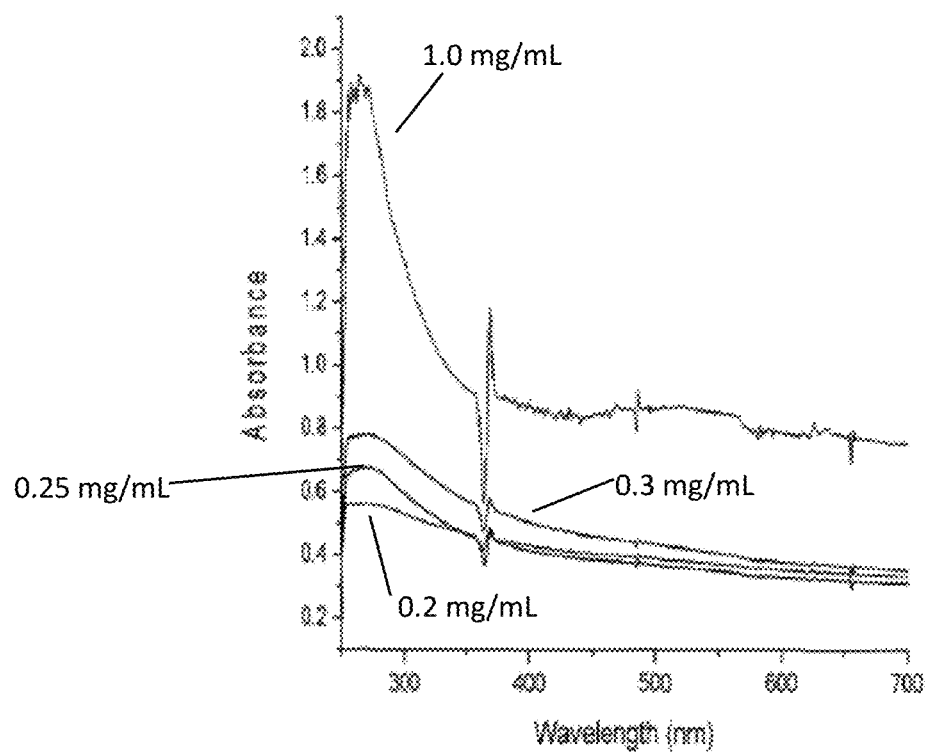
FIG. 7. Absorption spectra for GO-NTA as a function of concentration.

Previous work has shown that the typical GO sheet absorption band at ~240 nm is shifted to ~270 nm when the GO sheets are dispersed in aqueous solution. The origin of this hypsochromic shift is due to n-π* electronic transitions arising from the C=O bonds introduced by oxidation. GO-NTA samples prepared in this manner exhibited a major absorption peak at ~280 nm (FIG. 7), in good agreement with these reports.

Example 2. Graphene-Oxide Synthesis

GO was synthesized using an improved Hummers' method that is easier to execute, is higher yielding, and does not evolve toxic gases. It has been reported that there is no decrease in conductivity in the final product between the original and improved method, making it an attractive route for large scale production of GO [Marcano, D. C., et al. *ACS Nano* 2010 4, 4806-4814]. When a 9:1 mixture of $H_2SO_4$ and $H_3PO_4$ (130 mL total volume) was stirred with 1 g of graphite flakes (F516 flake graphite, 200-300 mesh, Asbury Carbons, Inc.) and $KMnO_4$ (6.0 g, 6.0 wt. equiv.), the reaction began with heating to ~40° C. and proceeded with further heating and stirring at 50° C. for 12 hours before cooling to 20° C. and pouring the reaction mixture into 120 mL of ice cold-water with 1 mL 30% $H_2O_2$. Next, this suspension was passed through a metal U.S. Standard testing sieve (W. S. Tyler, 300 μm) and then passed through a glass wool plug to filter larger particulates. The filtrate was then centrifuged at 4,000 rpm for 4 h, the supernatant discarded, and the pellet washed twice with a 1:1:1 volumetric ratio of $H_2O$, 30% HCl, and EtOH before passing the material through the testing sieve and centrifuging the filtrate at 4,000 rpm for 4 h to pellet the aggregated material. The supernatant was precipitated with $Et_2O$ (200 mL) and filtered through a 0.45 μm PTFE membrane to gather the solid. The final material was dried under a 15 μm vacuum for 12 h, yielding 1.8 g of GO.

Example 3. Graphene-Oxide-NTA Synthesis

GO was synthesized as described by Marcano et al. This intermediate (335 mg) was stirred in a mixture of $SOCl_2$ (60 mL) and DMF (1.5 mL) at 70° C. for 3 d before evaporating the $SOCl_2$ and DMF and washing the residue with dry DCM (3×50 mL). ACN (50 mL) and $Et_3N$ (3 mL) were then added and the mixture stirred for 30 min. Tris(O-t-butyl)-N$^α$,N$^α$-dicarboxymethyllysine ester (533 mg) was then added and the mixture stirred at 100° C. for 3 d before washing with THF and $H_2O$ (9,000 rpm for 15 min, 3 times for each solvent), before vacuum drying at 60° C. for 24 h. TFA (10 mL) in THF (30 mL) was added to the dried t-butyl-NTA ester intermediate (180 mg) and stirred at 60° C. for 5 h before washing with THF and $H_2O$ (11,000 rpm×15 min, 3 times for each solvent).

Example 4. GO-NTA Exfoliation

The GO-NTA sheets from Example 3 were ultrasonically exfoliated at 1 mg/mL by suspension of the powder in 5:1 MeOH:$H_2O$ using probe sonication at 150 watts for five cycles (45 s sonication followed by 45 s of rest in each cycle). The product was centrifuged at 1200 g for 10 min, after which the supernatant of exfoliated GO-NTA sheets was removed from the sediment of aggregated sheets and subjected to another 5 rounds of sonication. A final centrifugation at 1200 g for 10 min was performed prior to removal of the supernatant to yield a GO-NTA solution that was stored for subsequent grid coating experiments.

Example 5. Langmuir-Trough Setup

Exfoliated GO-NTA was deposited at the air-water interface of a Kibron μTrough via a syringe pump fitted with a 20 mL syringe. The GO-NTA dispersion was loaded into the syringe and slowly introduced at the air-water interface at a rate of 100 μL/min until the surface pressure reached 15 mN/m. The film was then allowed to relax for 5 min, followed by slow compression of the film to 15 mN/m. IPA was then added to the subphase and the film transferred to either Si wafers, bare 1500 mesh TEM grids, or holey carbon grids by L-S transfer.

Example 6. GO-NTA Monolayer Formation

Figure 3:
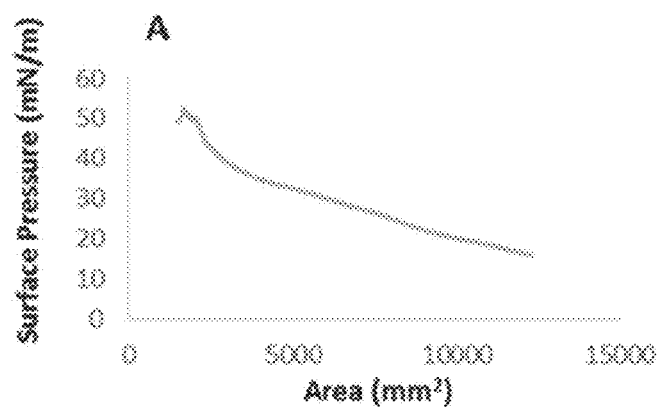
FIG. 3. Pressure-area isotherm for GO-NTA sheets at the air-water interface, dispersed at 67 ng/mL in water at 20° C. GO-NTA sheets compressed at a rate of 500 mm$^2$/min.

Compression of the GO-NTA material at the interface gave a characteristic surface pressure-area isotherm (FIG. 3), suggesting a progression from isolated GO-NTA sheets to close edge-to-edge packing of GO-NTA sheets, followed by folding, wrinkling, and sliding of the nearest neighbor GO-NTA sheets atop one another upon further compression, in a manner analogous to pressure-induced collapse of Langmuir phospholipid monolayer films. Repulsive electrostatic interactions and attractive van der Waals forces compete as GO-NTA sheets come into close contact. Previous work with GO monolayers has suggested that over-compression of GO causes irreversible coagulation above ~15 mN/m due to the increasing participation of attractive van der Waals interactions once the repulsive electrostatic interactions between sheet edges has been overcome by lateral compression. Transfer of these films onto silicon substrates at multiple surface pressures enabled the transfer of single layer GO sheets at surface pressures above 15 mN/m.

Example 7. 4-Aminobenzoic acid (PABA) Modification of GO-NTA

GO-NTA (1 mg/mL) was partially deactivated by adding PABA (30 mg) to a 10 mL GO-NTA dispersion. This mixture was probe sonicated at 150 W for 30 sec of continuous sonication, followed by shaking for 24 h on a rotary mixer. The PABA-GO-NTA was then exfoliated and washed as described above for GO-NTA exfoliation.

Example 8. Fluorescein Modification

Fluorescein modification of GO-NTA was performed by adding 2 mg of aminofluorescein to an aqueous solution of PABA-GO-NTA (10 mL at 1 mg/mL). This mixture was probe sonicated for 30 s at 150 W of continuous sonication and then placed on a rotary mixer in the dark for another 24 h. The material was then centrifuged to pellet the GO species before re-suspending in water, addition of 5:1 MeOH:$H_2O$, re-pelleted, and decanted a total of 10 times before exfoliation of the Fluorescein-PABA-GO-NTA (F-PABA-GO-NTA) product as described above for GO-NTA.

Example 9. Bovine Serum Albumin (BSA) Modification

Following L-S transfer of GO-NTA or PABA-GO-NTA onto EM grids and overnight drying in a desiccator, the grids were placed on a strip of Teflon before addition of BSA (10 µL of 0.1 mg/mL) and incubation for 5 min, followed by 3×20 µL double deionized H$_2$O washes. The modified grids were then stored in a desiccator until use.

Example 10. Fluorescence Microscopy Sample Preparation

F-PABA-GO-NTA was deposited onto 1500 mesh grids in the dark by L-S transfer as described above. After transfer, the grids were allowed to dry in the dark for 1 d before sandwiching them between a glass and cover slip with 5 µL of double deionized H$_2$O and the sandwich sealed with nail polish. The glass slide was then mounted on a light microscope for epifluorescence imaging.

Example 11. GO Concentration Measurements

The concentrations of the GO-NTA dispersions were measured at different steps of the synthesis by monitoring the UV-vis spectra of the products. Since each batch of GO-NTA has minor differences in concentration, each preparation was evaluated for its own experimentally determined extinction coefficient for subsequent concentration measurements. Standard solutions used to determine the extinction coefficients were prepared by dispersing a weighed amount of dry GO-NTA into known volumes of 5:1 MeOH:H$_2$O and measuring the absorbance at 280 nm across a series of dilutions with 5:1 MeOH:H$_2$O. The extinction coefficient was derived from the slope of these concentration-dependent absorption plots.

Example 12. GO-NTA Grid Treatment with Purified His$_6$-T7 Bacteriophage

Purified C-terminal gp10 His$_6$-T7 bacteriophage was initially prepared at a concentration of $10^{12}$ particles/mL, with dilution to $10^{10}$ particles/mL in HEPES buffer (pH=7.4) before application to the affinity grid surface. GO-NTA modified grids were placed on a Teflon strip, 1 mM NiSO$_4$ (10 µL) added and the grids incubated for 5 min before washing with double deionized H$_2$O (2×20 µL) and HEPES buffer (1×20 µL). Purified phage (3.5 µL) was then applied to the surface and incubated for 2 min before washing with HEPES (2×20 µL), double deionized H$_2$O (1×20 µL), and staining with 2% uranyl acetate (5 µL).

Example 13. GO-NTA Grid Treatment with His$_6$-T7 Bacteriophage Lysate

BL21 bacterial cells in 1 mL of LB media were grown to an OD of 0.8 before adding 1.0 µL of His$_6$-T7 bacteriophage (1×10$^{12}$ particles/mL) to the media and shaking the culture for 1 h. After bench top centrifugation of the cells, the supernatant was withdrawn for use in His$_6$-T7 bacteriophage particle capture studies. The grids were Ni$^{2+}$-activated as described above, except that His$_6$-T7 lysate (5 µL) was applied to the surface before incubation for 2 min. The grids were then washed with HEPES (2×20 µL), double deionized H$_2$O (1×20 µL), and then stained with 2% uranyl acetate (5 µL).

Example 14. GO-NTA Grid Treatment with His$_6$-GroEL Lysate

The ASKA Library was used to express N-terminal His$_6$-GroEL. Cells containing N-His$_6$-GroEL gene overexpression vector were grown to OD=0.6 (in 100 mL of LB broth using a 37° C. shaker/incubator) and induced with a final concentration of 1.0 mM IPTG, before allowing the cells to grow for an additional 4 h. After centrifugation and removal of the supernatant, the cell pellet was re-suspended in lysis buffer (20 mM HEPES, 100 mM NaCl, pH=7.4, 100 µg aprotinin, 174 µg phenylmethanesulfonyl fluoride (PMSF), and 500 µg of lysozyme) and allowed to sit for 20 min. Further disruption of the cell membranes was effected by 110 W probe sonication (35 pulses at 1 second/pulse), followed by centrifugation at 11,000 g for 10 min. The supernatant containing His$_6$-GroEL was diluted 10-fold and assayed for affinity binding using the Ni$^{2+}$-activation procedure described above, except that N-His$_6$-GroEL lysate (5 µL) was applied to the surface and incubated for 2 min. The grids were then washed and stained with 2% uranyl acetate as described above.

Example 15. Affinity Capture of His$_6$-GroEL from E. coli Lysates onto BSA-PABA-GO-NTA Grids for Cryo-EM Imaging Samples were prepared as described above for negative stain TEM imaging, except that BSA-PABA-GO-NTA modified grids were exposed to His$_6$-GroEL lysate, after which the excess solution was removed by blotting twice for 6 s per blot using an offset setting of −1 at 80% humidity using a Vitrobot device (FEI Company). The grids were then plunged into liquid ethane for cryofixation and imaged at 300 kV on an FEI Titan Krios equipped with a Gatan K2 Summit direct electron detection camera using low-dose techniques. Integrated microscope automation software Leginon was used to acquire a large set of micrographs at 11,000× magnification with an exposure time of 7.6 sec.

Example 16. Single Particle Analysis of His$_6$-GroEL

Direct electron detector movie frames were processed in Appion to produce a set of averaged, motion-compensated micrographs to be used in subsequent steps. The micrographs had a 1.32 Å$^2$/pixel resolution across a 4096 Å×4096 Å array. EMAN 2.1 software was used for reconstruction of 5363 particles that were manually picked from 217 micrographs using a box size of 256. Automatic contrast transfer function (CTF) estimation and structure factor were determined from the incoherent sum of particles using e2ctf and phase-flipped to generate high-pass CTF-corrected particle stacks. Defocus was estimated to range between 0.4 µm-4 µm, but 55% of the particles were defocused between 2 µm-3 µm which resulted in a somewhat jagged CTF slope. Particles were binned 2× for class averaging and 12 classes were chosen to create an initial model with imposed D7 symmetry. The classes contained a mix of top and side views. In the refinement steps, the input set of particles was divided into even/odd halves, each containing 2682 particles. Two independent refinements were generated, producing a gold standard of 8.1 Å (using 0.143 criteria) after 12 iterations over two refinements with an angular sampling of 1.76 degrees. Additionally, a Fourier shell correlation against an existing high-resolution cryo-EM map, EMD-5001 was performed. The maps were rotated and translated using Chimera to fit the volumes together. The correlation of this model against EMD-5001 (4.2 Å) gave an approximate resolution of 9 Å.

Example 17. Characterization of GO-NTA Monolayers

Epifluorescence microscopy, AFM, and SEM was employed to determine the thickness and lateral distribution of GO-NTA sheets deposited onto solid substrates by L-S transfer from the air-water interface. In particular, epifluorescence microscopy of F-PABA-GO-NTA monolayers revealed a monolayer-coated grid and negative control bare Cu TEM grid samples that showed significantly greater fluorescence intensity for grids coated with F-PABA-GO-NTA.

SEM and AFM analyses were performed after compression to 15 mN/m and L-S transfer of GO-NTA monolayer sheets onto Si wafers. To prepare Si wafers for L-S transfer, ~2.25 cm$^2$ wafers were cut and glued (bottom side) onto a transfer tube. The surface pressure was maintained until the Si wafer contacted the monolayer; the film was then recompressed to 15 mN/m after the L-S transfer step. The area difference before and after L-S transfer indicated transfer efficiencies of 75-85%. Image analysis of the coated Si wafers revealed the presence of GO-NTA monolayer sheets transferred from IPA-containing subphases with ~1.3 nm thicknesses that were relatively uniform, in good agreement with previously reported values for single layer GO. In the absence of IPA; however, data from SEM and AFM experiments revealed GO-NTA films comprised of overlapping sheets and undesirable layer thickness variations.

Figure 8:
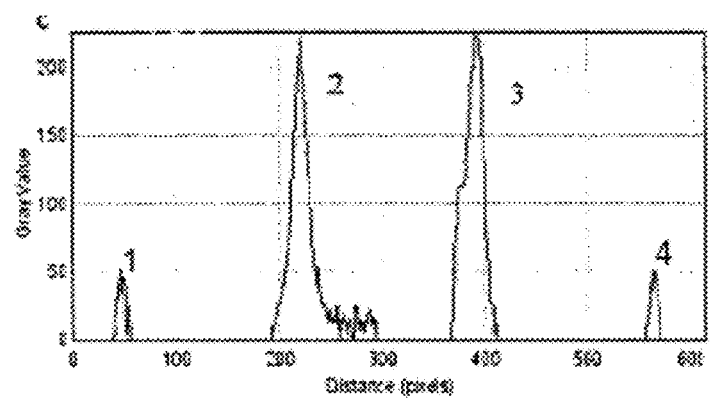
FIG. 8. Selected area electron diffraction analysis of GO-NTA film on a TEM grid.

Selected area electron diffraction analysis of GO-NTA L-S films, deposited onto bare 2000 mesh grids from the air-IPA/H$_2$O interface, revealed a hexagonal diffraction pattern, indicative of a single layer of graphenic material. The measured intensity of the inner (2,3) and outer (1,4) peaks confirms the presence of a single GO-NTA layer (FIG. 8).

Figure 4:
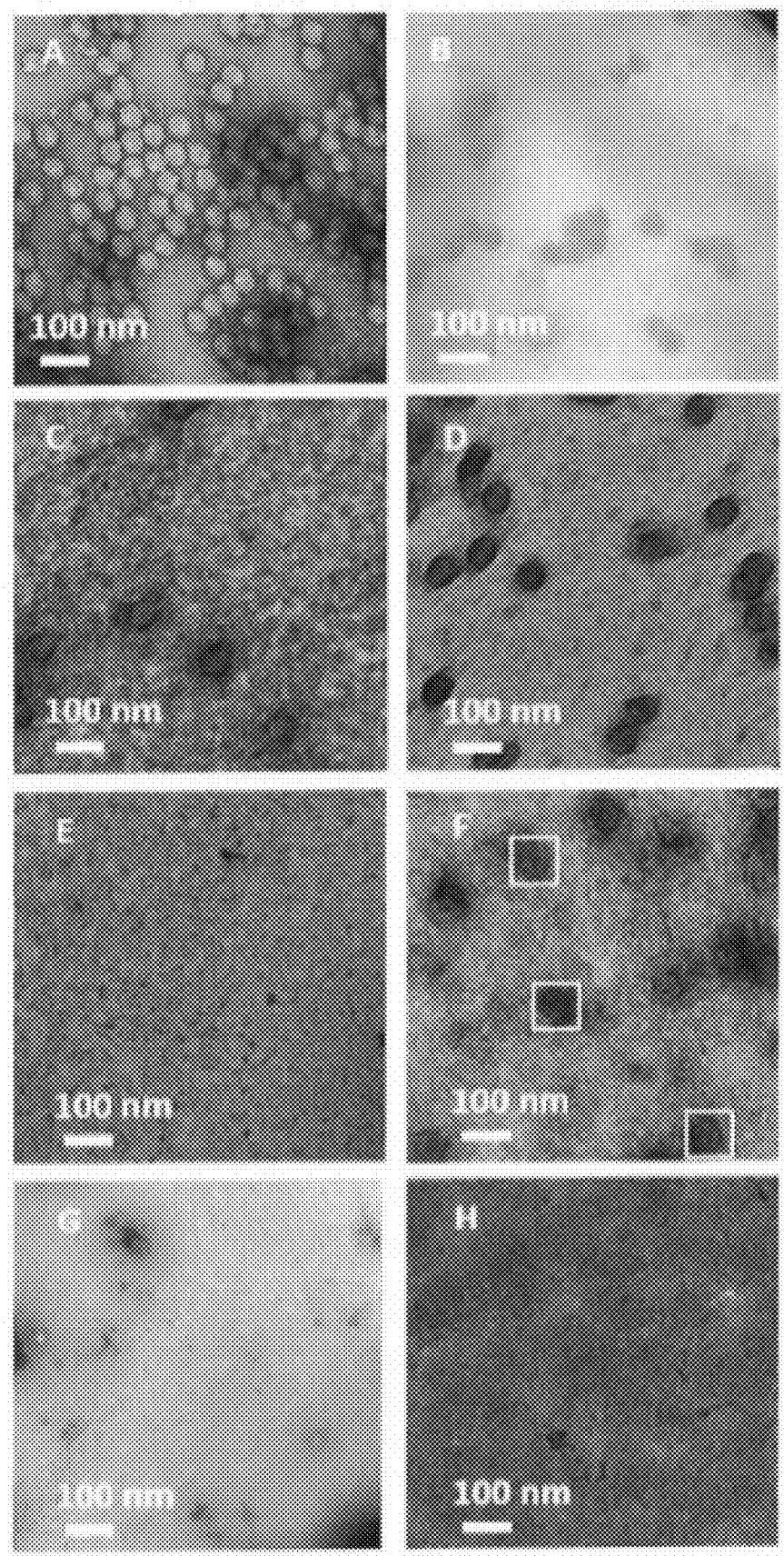
FIG. 4. Micrographs of negatively stained hiss-T7 bacteriophage using various TEM grid coatings: (A-B) GO-NTA; (C-D) PABA-GO-NTA; and (E-H) BSA-PABA-GO-NTA. Negative controls (A, C, E) demonstrate no capture of purified phage when $Ni^{2+}$ is absent, whereas coatings treated with $Ni^{2+}$ (B, D, F) show capture of purified phage. Affinity capture of phage from lysate (G) can be reversed by incubation of (G) with 500 mM imidazole (H) that removes the $Ni^{2+}$ from the coating and abrogates the affinity interaction between the phage and the grid surface.

EXAMPLE 18. Affinity Capture of His$_6$-T7 Bacteriophage from *E. coli* Lysate Using GO-NTA Monolayer Purification and PABA+BSA as Antifouling Agents. The capacity of GO-NTA coated grids to capture His$_6$-T7 bacteriophage (His$_6$-T7) by affinity interaction was examined first by negative-stain TEM. After a 2 min exposure of purified His$_6$-T7 on GO-NTA modified 1500 mesh grids, dense clusters of phage particles were found on the GO-NTA surface in the absence of Ni$^{2+}$ (FIG. 4A). GO-NTA was then treated with 4-aminobenzoic acid (PABA) after L-S transfer. The resulting PABA-GO-NTA grids showed a reduction in, but incomplete abrogation of, non-specific His$_6$-T7 binding under the same incubation conditions (FIG. 4C). When activated with Ni$^{2+}$, PABA-GO-NTA grids revealed a higher density of phage particles due to engagement of the NTA:Ni$^{2+}$:His$_6$ affinity interaction (FIG. 4D). The PABA-GO-NTA grids were incubated with BSA immediately before the affinity capture step. Under these conditions, BSA appears to complete the blockade of non-specific viral particle adsorption (FIG. 4E), suggesting that BSA inhibits non-specific binding more effectively here than PABA modification alone. After Ni$^{2+}$ activation of the BSA-blocked PABA-GO-NTA surfaces, a recovery in His$_6$-T7 binding to the grids (FIG. 4F) was observed. To further demonstrate the Ni$^{2+}$ dependence of this interaction, the grid was treated with 500 mM imidazole, which removes the Ni$^{2+}$ ion, leading to the elution of His$_6$-T7 from the grid. Taken together, these findings demonstrate the importance of deactivating highly reactive chemical functionalities on the surface of GO prior to use in affinity capture experiments.

Next, it was attempted to capture His$_6$-T7 directly, in that no additional processing other than centrifugation was used to remove undissolved components, from clarified *E. coli* lysate. The engineered His-tag does not interfere with His$_6$-T7 infectivity, thereby enabling the infection of BL21 cells and viral replication in vitro. A negative control experiment demonstrated that Ni$^{2+}$-free BSA-PABA-GO-NTA grids resulted in little or no capture of bacteriophage and minimal background adsorption from non-targeted cellular material; however, Ni$^{2+}$ activation prompted selective His$_6$-mediated binding of bacteriophage to the grid surface (FIG. 4G). As an additional control, the grid was washed with 500 mM imidazole after Ni$^{2+}$, but prior to incubation with lysate, to demonstrate that imidazole stripping of the metal ion results in the abrogation of His$_6$-T7 binding (FIG. 4H). These results indicate that BSA-PABA-GO-NTA coated grids are able to capture His$_6$-T7 directly from clarified lysate on the grid using the NTA:Ni$^{2+}$:His$_6$ affinity interaction.

Figure 5:
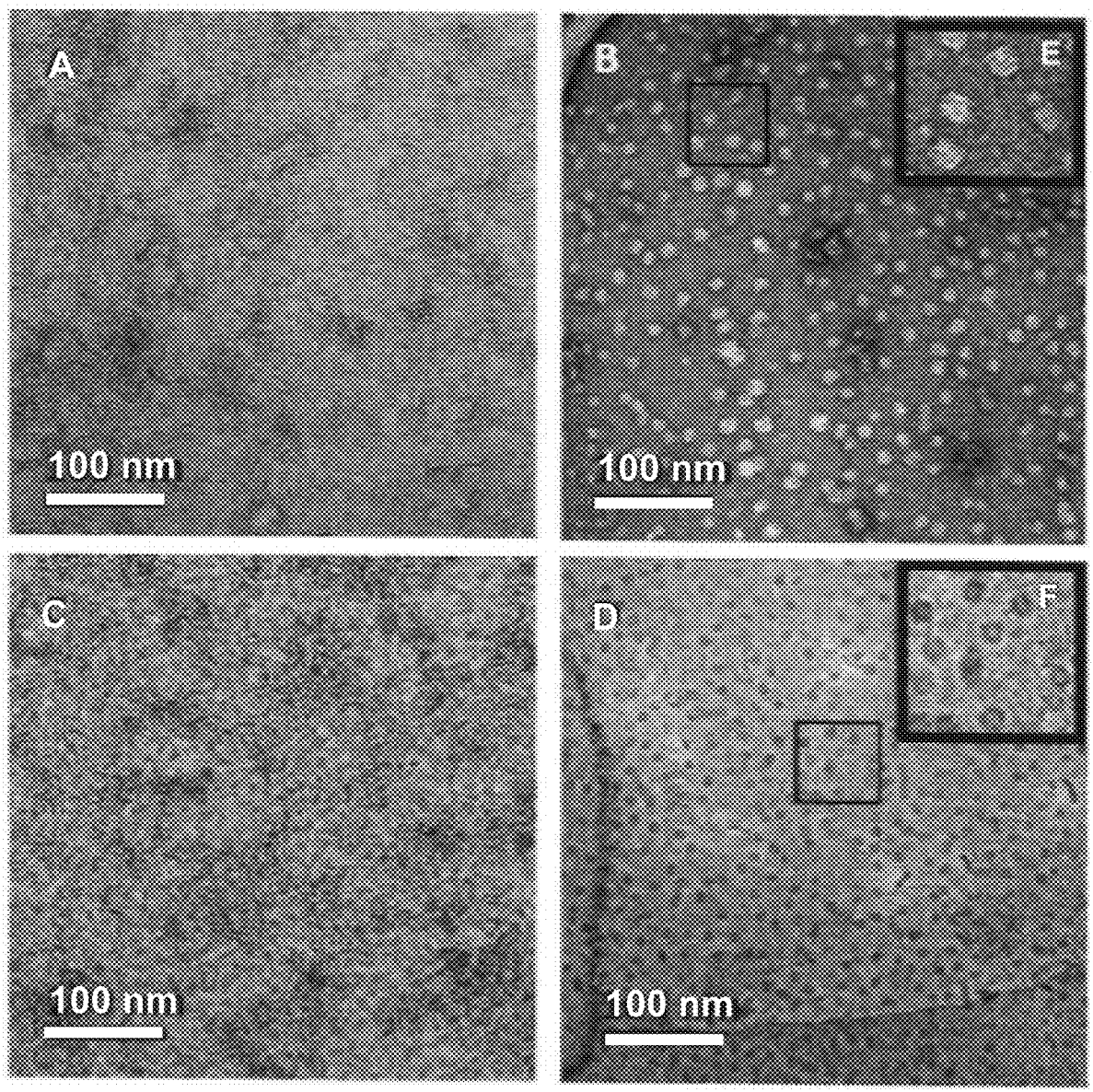
FIG. 5. Micrographs of hiss-GroEL lysate affinity capture using BSA-PABA-GO-NTA TEM grid coating. Micrographs (A-C) are negatively stained. (A) Negative control showing no capture of hiss-GroEL when $Ni^{2+}$ is absent. (B) Affinity coating activated with $Ni^{2+}$ displays specific capture of hiss-GroEL from lysate with (E) being an enlarged portion of the adjacent boxed region. Treatment of the grid in (B) with 500 mM imidazole (C) leads to $Ni^{2+}$ stripping from the coating and abrogation of hiss-GroEL capture. (D) Representative cryo-EM image of affinity captured hiss-GroEL from lysate with (F) being an enlarged portion of the adjacent boxed region.

Example 19. Affinity Capture of GroEL From *E. coli* Lysate Using BSA-PABA-GO-NTA Monolayer Purification The performance of antifouling BSA-PABA-GO-NTA coatings for high-resolution single particle reconstruction analysis was evaluated by performing on-grid affinity capture of His$_6$-GroEL from *E. coli* lysates. As observed for His$_6$-T7 capture, specific binding of His$_6$-GroEL occurred only with Ni$^{2+}$-activated (FIG. 5B), but not Ni$^{2+}$-free (FIG. 5A) or 500 mM imidazole treated grids (FIG. 5C). Cryo-EM images of His$_6$-GroEL deposited onto BSA-PABA-GO-NTA coated grids were obtained (FIG. 5D). Initial attempts at His$_6$-GroEL capture and cryofixation on 1500 mesh grids coated with BSA-PABA-GO-NTA generated unacceptably thick sample vitrification; however, high quality samples of His$_6$-GroEL captured from lysate were afforded by BSA-PABA-GO-NTA films deposited by L-S transfer onto lacey carbon-supported 400 mesh copper grids.

Example 20. Single Particle Analysis of His$_6$-GroEL

EMAN 2.1 was used for single particle analysis of His$_6$-GroEL deposited onto BSA-PABA-GO-NTA coated grids since this protein target is often used for gauging workflow performance and data processing robustness. The reconstruction effort followed the usual steps from within the application, except that the particles were manually picked. Background signal contributions by the BSA blocking layer may also have contributed to the difficulties encountered during attempts at automated particle picking. Nonetheless, 5363 particles were hand-picked from 217 micrographs and the particles rapidly converged into coherent classes displaying high contrast (FIG. 6A).

Figure 6:
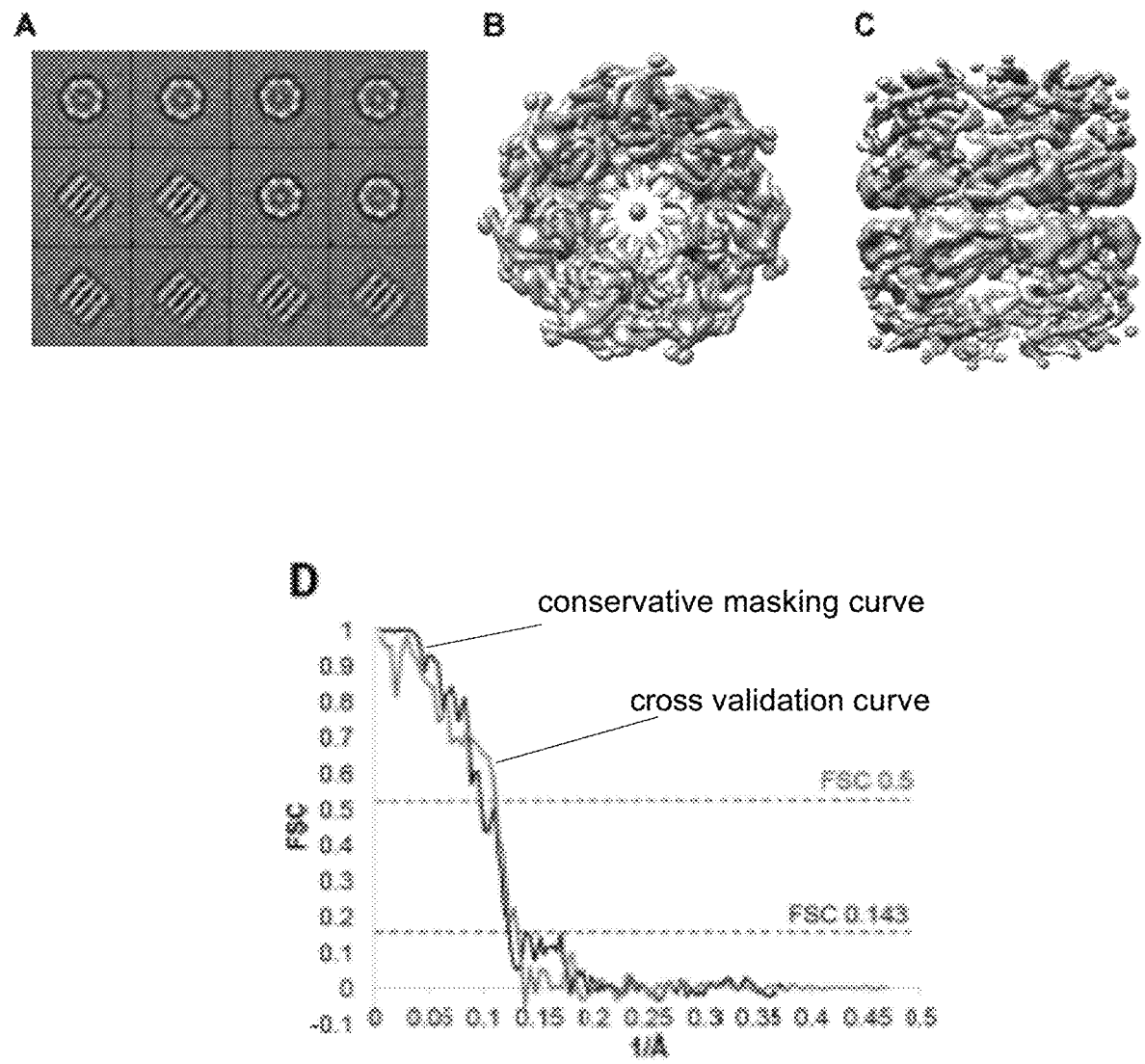
FIG. 6. (A) Class averages of hiss-GroEL images captured from BSA-PABA-GO-NTA coated grids that were used to build the initial model; (B) Top and (C) side views of refined hiss-GroEL EM map at 8.1 Å resolution (gold standard, 0.143 criteria); (D) Fourier Shell Correlations: conservative masking, and cross-validation curves between published GroEL map EMD-5001 and the map of the disclosure.

Of 50 total class averages, 12 were chosen to produce an initial model with imposed D7 symmetry (FIG. 6A). After 12 refinement iterations with an angular sampling of 1.76 degrees, we were able to produce a gold standard (0.143 criteria) density map having 8.1 Å resolution using conservative masking (FIGS. 6B-D). There were visible nodes in the FSC curve at regular intervals that resulted from an uneven distribution of micrograph defocuses.

To verify the accuracy of the model, a comparison with published 4.2 Å resolution cryo-EM map EMD-5001 that was also produced by EMAN using D7 symmetry. Chimera was used to fit the volumes before calculating the FSC, yielding a 9 Å resolution using 0.5 criteria (FIG. 6D). As noted in FIG. 6D, the conservative masking and the cross validation curves are good fits at 0.5 FSC and 0.143 FSC, which are accepted standards in the field.

A substantial difference between the map and the published structure was observed, herein additional electron density within the inner pore of the protein was found in the case of the HiseGroEL map. This finding is attributable to the extended amino acid sequences at the N- and C-termini (i.e., MRGSHEIREIHHTDPALRA (SEQ ID NO: 5) and GLCGR (SEQ ID NO: 6), respectively) of our HiseGroEL construct derived from the ASKA Library, which is not present in the published structure. When taking that difference into account, however, the fit was good as indicated in FIG. 6D.

Wild type N- and C-termini of the protomers are located at the surface of the inner pore lining the assembled tetradecameric complex. Thus, the 14 engineered subunits comprising the $His_6$-GroEL complex yield an additional 308 residues that occupy the pore, of which 84 are histidines. Given the large number of potential metal chelation regioisomers and topoisomers, as well as the high potential for conformational flexibility in the N- and C-terminal sequences, this density is unlikely to adopt a defined structure and instead appears as a filled "droplet" within each ring. Also, there is a noticeable decrease in density in the flexible apical region that suggests less structural coherency. From these findings, it is inferred that the additional pore residues, along with NTA chelation, may create dynamic distortions to the structure of GroEL that could vary for each particle, reducing coherency and map density at the apical ends.

Example 21. Langmuir-Schaefer Film Deposition onto Graphene-Bearing Grids

Stock solutions of two lipid mixtures (e.g., $Ni^{2+}$:NTA-poly(ethylene glycol 2000)-1,2-distearoyl-sn-3-glycerophosphoethanolamine (capture agent) and methoxy-poly(ethylene glycol 350)-1,2-distearoyl-sn-3-glycerophosphoethanolamine (deactivating agent)) in proportions appropriate for the desired surface density of target protein (e.g., 1:99-1:5 capture ligand lipid:blocking lipid ratio) are prepared in $CHCl_3$ at 2.0 mg/mL and stored at −80° C. These solutions are spread at the air-water interface of a monolayer trough via 10 μL microsyringe and compressed to a final surface pressure of 30-45 mN/m. The compressed lipid monolayers are then deposited onto Graphenea Quantifoil Gold TEM grids or other suitable TEM grid bearing a graphene monolayer by Langmuir-Schaefer transfer. The LS film was then dried and transferred to a standard TEM grid box for later use.

Example 22. General Guidelines for Sample Incubation on Affinity Grids

The observed sample capture efficiency is a function of the target protein concentration, the target protein molecular weight, and the surface density of capture ligand. Approximate incubation times at 25° C. for a given target protein concentration are summarized below; however, the actual times required for optimal binding will depend on total protein concentration, sample viscosity, competing ligand concentrations, and sample incubation temperature.

| 35 kD Target    | 0.1 mg/mL | 0.5 mg/mL | 1.0 mg/mL | 2 mg/mL |
|---|---|---|---|---|
| 1% capture agent | 15 min | 10 min | 5 min | 2 min |
| 5% capture agent | 5 min  | 2 min  | 1 min | 30 sec |

| 100 kD Target    | 0.1 mg/mL | 0.5 mg/mL | 1.0 mg/mL | 2 mg/mL |
|---|---|---|---|---|
| 1% capture agent | 20 min | 14 min | 7 min | 4 min |
| 5% capture agent | 7 min  | 4 min  | 2 min | 1 min |

| 300 kD Target    | 0.1 mg/mL | 0.5 mg/mL | 1.0 mg/mL | 2 mg/mL |
|---|---|---|---|---|
| 1% capture agent | 30 min | 20 min | 10 min | 5 min |
| 5% capture agent | 10 min | 7 min  | 5 min  | 3 min |

| ≥1 mD Target     | 0.1 mg/mL | 0.5 mg/mL | 1.0 mg/mL | 2 mg/mL |
|---|---|---|---|---|
| 1% capture agent | 45 min | 35 min | 25 min | 15 min |
| 5% capture agent | 15 min | 12 min | 8 min  | 5 min |

Example 23. Synthesis of Specific Compounds—General. Materials

Solvents were purchased from Mallinckrodt/Baker and used without further purification unless noted. Toluene was purchased from Fisher. N-(3-dimethylaminopropyl)-N'-ethylcarbodiimide hydrochloride (EDC) and $N^\varepsilon$-((benzyloxy)carbonyl)-1-lysine (H-Lys(Z)—OH) were purchased from Advanced Chemtech. Heterobifunctional PEG derivatives were purchased from JenKem technology USA. 1,2-distearoyl-sn-glycero-3-phosphoethanolamine (DSPE) and 1,2-(tricosa-10',12'-diynoyl)-sn-glycero-3-phosphoethanolamine (DTPE) were purchased from Avanti Polar Lipids. All other chemicals were purchased from Sigma Aldrich and used without further purification. Dichloromethane (DCM), and toluene were distilled from $CaH_2$. Triethylamine (TEA) was distilled from $CaH_2$ and stored over BaO. Tetrahydrofuran (THF) was distilled from sodium-benzophenone ketyl. α-methoxy-polyethylene glycol (mPEG350) was purchased from Sigma Aldrich and purified by azeotropic drying with toluene. Jones' reagent (1.25 M in $CrO_3$) was prepared by dissolving 17.5 g $CrO_3$ in 125 mL water plus 16 mL conc. $H_2SO_4$.

Experimental Methods. Nuclear magnetic resonance spectroscopy (NMR) was performed on a Bruker Avance ARX-400 NMR spectrometer using deuterated chloroform ($CDCl_3$) as NMR solvent and internal standard unless otherwise noted.

Example 24. Synthesis of mPEG350-DTPE

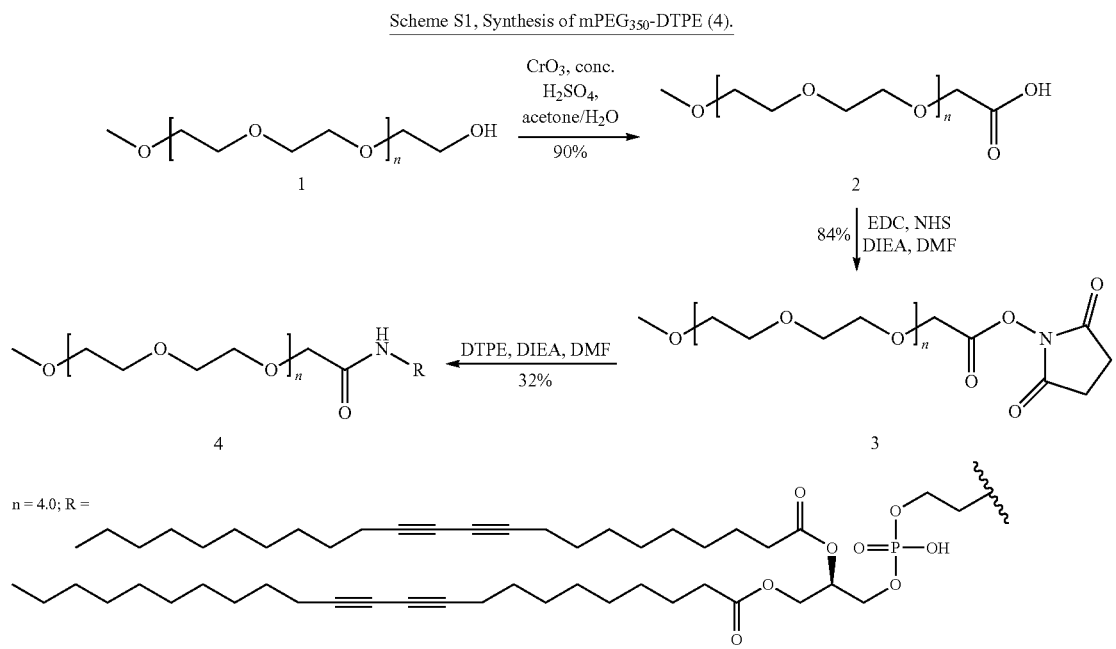

mPEG350-CO₂H (2). mPEG350 (1, 5.00 g, 14.3 mmol) was dissolved in 280 mL acetone. Jones' Reagent (15 mL, 1.25 M, 18.75 mmol) was added to a 500 mL round bottom flask and the mPEG solution was added to this flask dropwise over 1 h via addition funnel. The resulting solution was stirred at 20° C. for 1 h before quenching the excess Jones reagent with 10 mL iPrOH. The resulting green precipitate was removed by decantation of the liquid solution. The volatiles were removed under reduced pressure and the residue dissolved in 100 mL H₂O. The aqueous phase was extracted with DCM (3×120 mL). The organic layers were combined and dried over anhydrous Na₂SO₄, filtered, and evaporated under reduced pressure. The clear oily residue was used without further purification. Yield: 4.52 g (90%); TLC: $R_f$=0.26 (3:17 MeOH:DCM); ¹H NMR (400 MHz, CDCl₃): δ 3.35 (s 3H), 3.4-3.8 (m 30H), 4.01 (s 2H), 10.1-12.2 (br 1H).

mPEG350-NHS (3). Compound 2 (274 mg, 0.753 mmol), and NHS (217 mg, 1.885 mmol) were dissolved in 15 mL DCM and the resulting solution was cooled in an ice bath. EDC (173 mg, 0.902 mmol) was then added followed by DIEA (393 µL, 2.259 mmol), and the solution was stirred while slowly warming from 4 to 20° C. over 18 h. Volatiles were removed under reduced pressure and the residue was dissolved in 50 mL DCM. The organic filtrate was washed with 50 mL H₂O twice before combining and extracting the aqueous phase with DCM (2×20 mL). The combined organic phases were dried over anhydrous Na₂SO₄ before removing the solvent under reduced pressure and purifying the residue by flash chromatography on silica (3:17 MeOH:DCM). Yield: 230 mg (84%); TLC: $R_f$=0.66 (3:17 MeOH:DCM); ¹H NMR (400 MHz, CDCl₃): δ 2.65 (s 4H), 3.35 (s 3H), 3.4-3.8 (m 30H), 4.01 (s 2H).

mPEG350-DTPE (4). Compound 3 (100 mg, 0.210 mmol) and DTPE (183 mg, 0.210 mmol) were dissolved in DMF (5 mL) in a 100 mL round bottom flask covered in aluminum foil. DIEA (37 µL) was added and the solution was stirred at 20° C. for 36 h under N₂. The volatiles were removed under reduced pressure and the residue was purified by chromatography on silica (3:17 MeOH:DCM). Yield: 82 mg (32%); TLC: $R_f$=0.29 (3:17 MeOH:DCM). ¹H NMR (400 MHz, CDCl₃): δ 0.88 (t 6H), 1.25-1.35 (m 44H), 1.49 (m 8H), 2.22 (m 8H), 2.53 (br 2H), 2.61 (br 2H), 3.36 (s 3H), 3.54-4.32 (m, 40H), 512 (br 1H), 7.64 (br 1H).

Example 25. Synthesis of NTA Derivatives

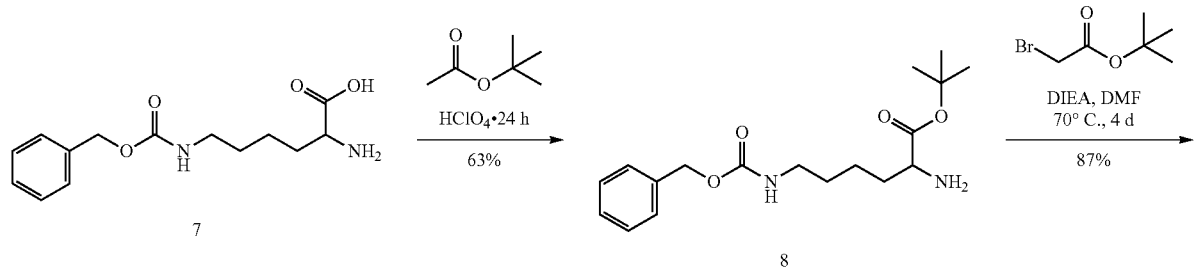

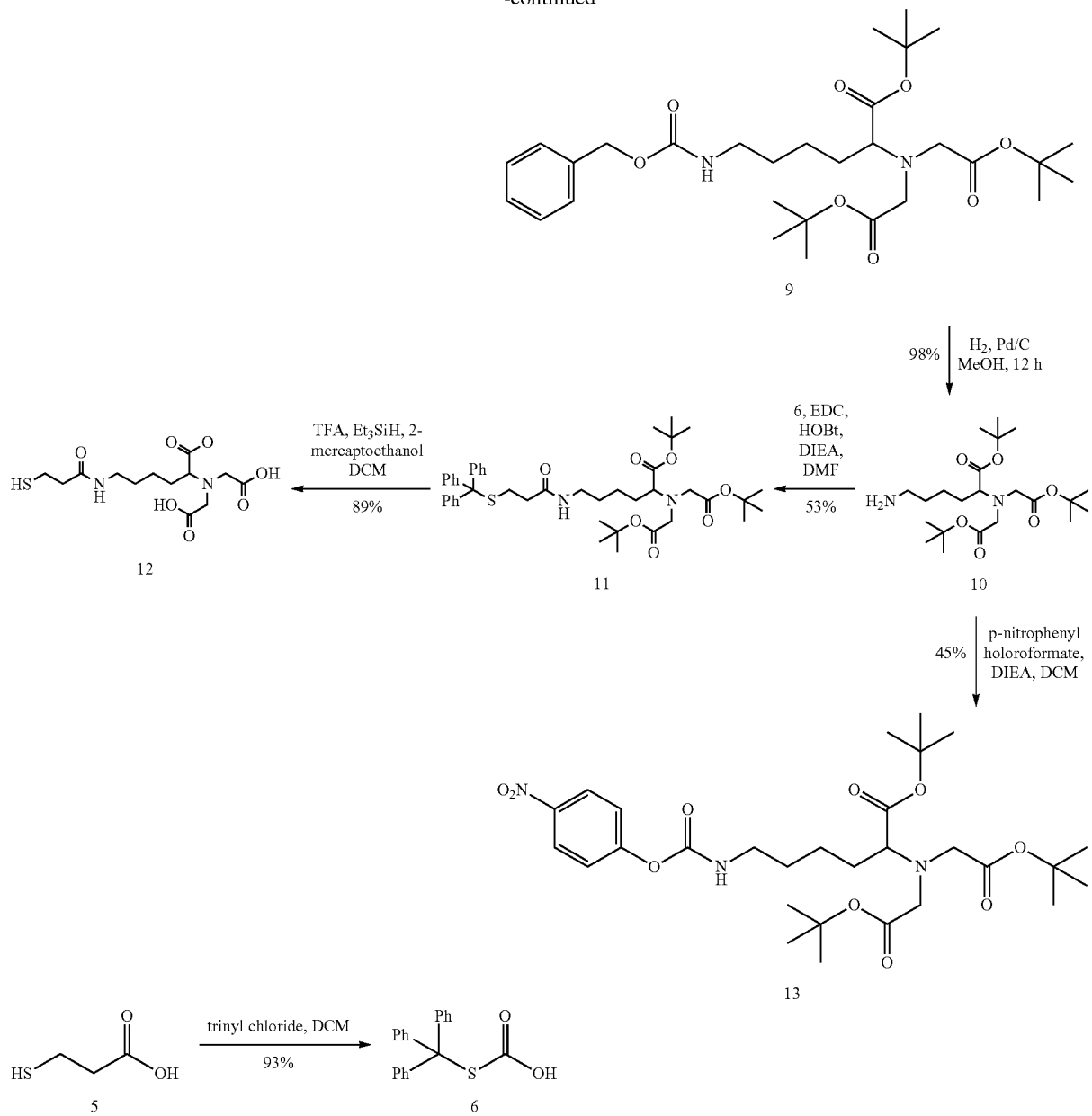

S-Trityl-3-mercaptopropionic acid (6). 3-Mercaptopropionic acid (5, 6.00 g, 56.5 mmol) was dissolved in DCM (50 mL) in a 250 mL round bottom flask. Trityl chloride (17.34 g, 62.2 mmol) in DCM (30 mL) was added dropwise to this solution over 1 h before stirring for an additional 12 h. The white precipitate was filtered and washed with diethyl ether (2×50 mL) and dried under a 50 µm vacuum to give a fine white powder. Yield: 18.25 g (93%); $^1$H NMR (400 MHz, CDCl$_3$): δ 2.25 (t, 2H, J=8 Hz), 2.47 (t, 2H, J=8 Hz), 7.2-7.3 (m, 9H), 7.43 (d, 6H).

tert-Butyl N6-((benzyloxy)carbonyl)-l-lysinate (8). N$^ε$-((benzyloxy)carbonyl)-l-lysine (12.03 g, 42.92 mmol) was mixed with t-butyl acetate (120 mL) in a 250 mL round bottom flask and concentrated HClO$_4$ (3.90 mL) added to this mixture, producing a clear solution. This solution was stirred for 12 h before extracting with 200 mL H$_2$O, 200 mL 5% HCl, then 200 mL H$_2$O. The aqueous extracts were combined and extracted with diethyl ether (3×200 mL) after addition of 30% NaOH solution until the aqueous layer was pH 11. The ether extracts were combined and dried over anhydrous MgSO$_4$. The ether was then filtered and concentrated under reduced pressure and dried under a 50 µm vacuum overnight giving a colorless oil. Yield: 9.25 g (63%). $^1$H NMR (400 MHz, CDCl$_3$): δ 1.30 (s 9H), 1.23-1.50 (m 8H), 2.99 (t 2H), 3.11 (t (1H), 4.91 (s 2H), 5.61 (br 1H), 7.14-7.16 (m 5H). 13C NMR (101 MHz, CDCl$_3$): δ 175.18, 156.34, 142.38, 136.60, 128.31, 127.88, 108.60, 80.74, 77.46, 77.14, 76.82, 66.29, 54.66, 40.66, 34.36, 31.08, 29.53, 27.90, 22.64.

Di-t-butyl 2,2'-((6-(((benzyloxy)carbonyl)amino)-1-(t-butoxy)-1-oxohexan-2-yl)azanediyl)diacetate (9). NE-Benzyloxycarbonyl-L-lysine-t-butyl ester (8, 9.25 g, 27.5 mmol) was dissolved in DMF (70 mL) prior to the addition of t-butyl bromoacetate (12.2 mL, 16.10 g, 82.6 mmol) and DIEA (16.8 mL, 11.9 g, 92.1 mmol) by syringe. The solution was stirred under N2 at 70° C. for 72 h. The solvent was evaporated under reduced pressure and the residue was extracted with 200 mL of ethyl acetate and filtered. The ethyl acetate extract was purified by flash chromatography on silica (4:1 hexane:EtOAc) to give 9 as a slightly yellow oil. Yield: 12.56 g (87%); TLC: Rf=0.48 (4:1 hexane:EtOAc); $^1$H NMR (CDCl$_3$): δ 1.25-1.50 (m 6H), 1.30 (s 18H), 1.32 (s 9H), 3.04 (m 2H), 3.16 (t 1H), 3.33 (q 4H), 4.93 (s 2H), 5.39 (br 1H), 7.15-7.19 (m 5H). $^{13}$C NMR (101 MHz, CDCl$_3$) δ 172.07, 170.41, 156.32, 136.69, 128.15, 127.79, 127.64, 80.70, 80.33, 77.54, 77.22, 76.90, 66.03, 64.91, 60.04, 53.62, 40.56, 29.93, 29.02, 27.97, 27.86, 27.73, 22.80, 20.71, 13.97.

Di-t-butyl 2,2'-((6-amino-1-(tert-butoxy)-1-oxohexan-2-yl)azanediyl)diacetate (10). Compound 9 (9.84 g, 17.4 mmol) was dissolved in MeOH (90 mL) in a 500 mL round bottom flask. To this solution was added 40 mg of 10% Pd/C. The flask was evacuated and purged with H$_2$ three times and then stirred for 12 h under 1 atm H$_2$. The heterogeneous solution was then filtered through a pad of Celite, with further washing of the Celite cake with 50 mL MeOH. The filtrate was concentrated under reduced pressure to give 10 as a clear oil. Yield: 7.35 g (98%); TLC: Rf=0 (4:1 hexane:EtOAc); $^1$H NMR (CDCl$_3$): δ 1.29 (s 18H), 1.30 (s 9H), 1.1-1.5 (m 6H), 2.63 (t 2H), 3.16 (t 1H), 3.30 (q 4H), 3.96 (br 3H)$^{13}$C NMR (101 MHz, CDCl$_3$) δ 172.05, 170.46, 80.78, 80.42, 77.41, 77.09, 76.77, 64.94, 53.52, 49.54, 40.90, 31.09, 30.09, 27.95, 27.87, 22.91.

Di-t-butyl 2,2'-((1-(t-butoxy)-1-oxo-6-(3-(tritylthio)propanamido)hexan-2-yl)azanediyl)diacetate (11). Compound 10 (1.46 g, 4.19 mmol) and Compound 6 (1.80 g, 4.19 mmol) were dissolved in DMF (100 mL) in a 250 mL round bottom flask. This solution was cooled on an ice bath before addition of EDC (0.962 g, 5.02 mmol), HOBt (0.678 g, 5.02 mmol), and 1.86 mL of DIEA (1.35 g, 10.4 mmol). The solution was stirred under Ar for 48 h while allowing the mixture to gradually warm from 4→20° C. The DMF was evaporated under reduced pressure and the residue was dissolved in EtOAc (80 mL). This solution was washed with H$_2$O (2×100 mL) before combining the aqueous phases and back extracting with EtOAc (100 mL). The EtOAc layers were combined and dried over anhydrous Na$_2$SO$_4$. The solvent was evaporated and the residue purified by flash chromatography on silica using 1:1 hexane:EtOAc as eluent yielding 11 as a colorless oil. Yield: 1.70 g (53%); TLC: Rf=0.54 (1:1 hexane:EtOAc); $^1$H NMR (CDCl$_3$): δ 1.22-1.61 (m 6H), 1.39 (s 18H), 1.43 (s 9H), 2.09 (t 2H), 2.46 (t 2H), 3.11 (m 2H), 3.25 (t 1H), 3.43 (m 4H), 5.98 (br 1H), 7.14-7.4 (m 15H); MS (ESI+). Expected: 762.02 [M+H]; Found 762.71.

2,2'-((1-Carboxy-5-(3-mercaptopropanamido)pentyl)azanediyl)diacetic acid (12). Compound 11 (0.800 g, 1.05 mmol) was dissolved in DCM (10 mL), followed by addition of Et$_3$SiH (0.367 g, 3.16 mmol) and 2-mercaptoethanol (0.246 g, 3.15 mmol). This solution was cooled on an ice bath before addition of TFA (15 mL) dropwise over 10 min. The solution was stirred for 1 h at 4° C. before removal of the volatiles under reduced pressure. Diethyl ether (20 mL) and 4 drops of concentrated HCl were added to the residue before decanting the organic phase and repeating the process two more times. Toluene (30 mL) was then added to the residue and evaporated under reduced pressure three times to give compound 12 as a white powder. Yield: 0.327 g (89%); $^1$H NMR (D$_2$O): δ 1.41 (m 2H), 1.49 (m 2H), 1.80-1.90 (m 2H), 2.43 (t 2H), 2.67 (t 2H), 2.73 (m 1H), 3.13 (m 2H), 3.93 (s 4H).

Di-tert-butyl-2,2'-((1-(tert-butoxy)-6-(((4-nitrophenoxy)carbonyl)amino)-1-oxohexan-2-yl)azanediyl)diacetate (13). p-nitrophenyl chloroformate (PNP—Cl, 0.552 g, 2.74 mmol) was dissolved into 20 mL DCM in a 100 mL round bottom flask equipped with a stir bar and addition funnel and was cooled to 4° C. in an ice bath. Compound 12 (0.983 g, 2.28 mmol) in 20 mL DCM was added to the addition funnel. The system was evacuated and flashed with nitrogen gas. The solution of 12 was added over a one hour period at 4° C. and stirred for an additional 12 hours warming to room temperature. The solution was concentrated in vacuo and purified by flash chromatography using 4:1 hexanes:EtOAc as eluent. Yield: 0.609 g (45%); TLC: Rf=0.24 (4:1 hexanes:EtOAc); $^1$H NMR (CDCl$_3$): δ 1.38 (s 18H), 1.40 (s 9H), 1.18-1.59 (m 6H), 3.18-3.29 (m 3H), 3.40 (q 4H), 6.09 (br 1H), 7.24 (d 2H, J=9 Hz), 8.14 (d 2H, J=9 Hz); MS (ESI+). Expected: 596.68 [M+H]; Found 596.59 ([M+H], 618.54 [M+Na].

Example 26—Synthesis of NTA-PEG2000-DSPE

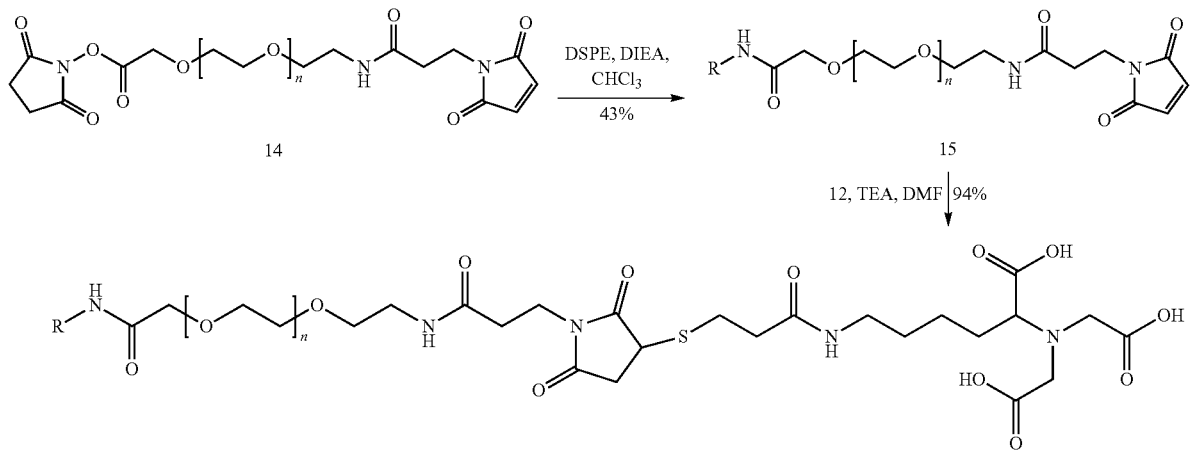

Scheme S3. Synthesis of NTA-PEG2000-DSPE (16).

n = 45, R =

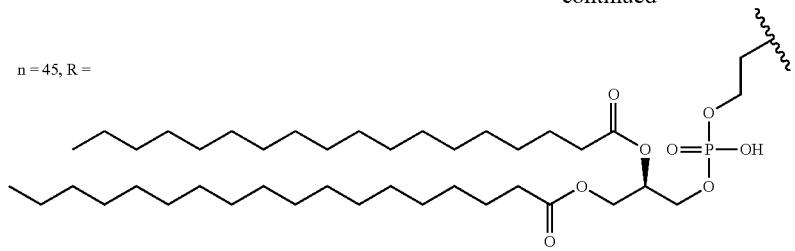

Maleimide-PEG2000-DSPE (15). DSPE (0.072 g, 0.096 mmol) and NHS-PEG2000-maleimide (0.200 g, 0.095 mmol) were dissolved in CHCl$_3$ (15 mL) in a 50 mL round bottom flask with stir bar and DIEA (0.062 g, 0.480) mmol was added via syringe. The flask was evacuated and flushed with nitrogen and stirred for 72 hours at ambient temperature. The volatiles were evaporated under reduced pressure and the residue purified by flash chromatography on silica using a gradient starting with 85:15 DCM:MeOH and increasing in polarity to 80:20 DCM:MeOH. Yield: 0.118 g (43%); TLC: Rf=0.48 (4:1 DCM:MeOH); $^1$H NMR (CDCl$_3$): δ 0.84 (t 6H), 1.15-1.40 (m 64H), 2.24 (m 4H), 2.48 (t 2H) 2.99 (m 2H), 3.37-4.10 (m 180H), 3.80-3.96 (m 4H), 4.12 (m 2H), 4.34 (d 2H), 5.17 (m 1H), 6.27 (br 1H), 6.67 (s 1H), 7.38 (br 1H).

NTA-PEG2000-DSPE (16). Compounds 15 (20.0 mg, 0.007 mmol) and 12 (18.0 mg, 0.051 mmol) were dissolved in DMF (4 mL) in a 25 mL round bottom flask with stir bar. TEA (15.0 μL, 0.119 mmol) was added and the flask was evacuated and flushed with nitrogen. The solution was stirred at 40° C. for 24 hours monitoring the consumption of starting material by TLC. Volatiles were removed in vacuo at 45° C. the residue was dissolved in 6 mL PBS buffer (pH=7.2) plus 4 mL MeOH. This solution was extracted with CHCl$_3$ (3×15 mL). The organic extracts were combined and dried over anhydrous Na$_2$SO$_4$, filtered and concentrated in vacuo to give 16. Yield: 21.2 mg (94%); TLC: Rf=0.0 (4:1 DCM:MeOH); $^1$H NMR (CDCl$_3$): δ 0.84 (t 6H), 1.15-1.40 (m 64H), 2.25 (s 4H), 2.28-2.32 (m 2H), 2.48-2.53 (m 2H), 2.75-2.78 (m 4H), 2.48-3.7 (m 180H), 3.70 (s 4H), 3.88 (br 2H), 4.00 (br 2H), 4.16 (br 2H), 4.37-4.40 (br 1H), 5.30 (s 1H), 6.96 (s 1H).

Example 27. Synthesis of NTA-PEG200-DTPE

Scheme S4. Synthesis of NTA-PEG2000-DTPE (21).

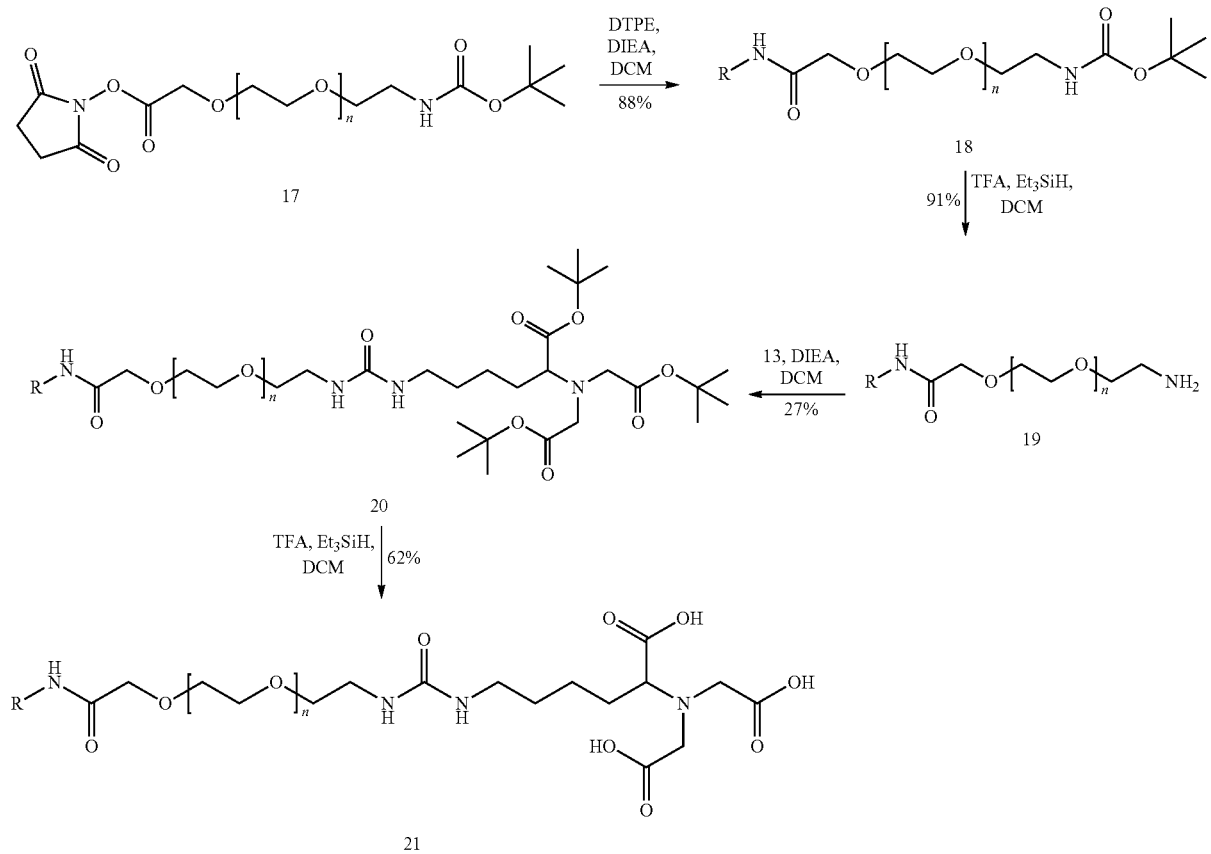

n = 45, R = 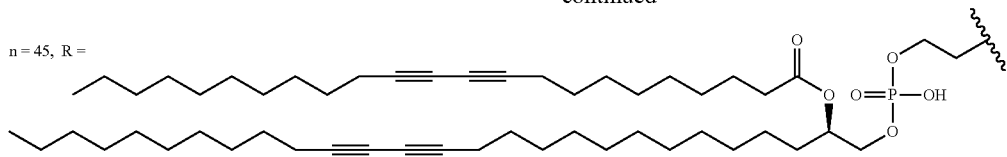

NHBoc-PEG2000-DTPE (18). NHS-PEG2K-NHBoc (17, 190 mg, 0.095 mmol) and DTPE (82.8 mg, 0.095 mmol) were dissolved in DCM (10 mL) in a 25 mL round bottom flask with stir bar. DIEA (83 µL, 0.474 mmol) was added and the flask was evacuated, flushed with nitrogen and covered with aluminum foil. The solution was stirred at ambient temperature for 48 hours in the dark. Evaporated volatiles and purified by flash chromatography on silica using an eluting system of DCM and MeOH starting with 95:5 then 90:10 then 85:15. Fractions containing product were combined and dried in vacuo to give 18. Yield: 0.209 g (88%); TLC: $R_f$=0.72 (80:20 DCM:MeOH); $^1$H NMR (CDCl$_3$): δ 0.88 (m 6H), 1.23-1.49 (m 50H), 1.42 (s 9H), 2.21 (m 8H), 2.66 (t 4H), 3.26-3.96 (m 180H), 4.11-4.12 (m 2H), 4.33-4.36 (m 2H), 5.17 (br 1H).

NH$_2$—PEG2000-DTPE (19). Compound 18 (209 mg, 0.076 mmol) and triethylsilane (200 µL, 1.25 mmol) was dissolved in 30% TFA in DCM solution (20 mL) and stirred for 1.5 hours under ambient temperature and atmosphere. Volatiles were removed in vacuo and the residue was evaporated with 15 mL DCM twice more. The product was dried in vacuo and used without further purification. Yield: 0.191 g (91%); TLC: $R_f$=0.56 (80:20 DCM:MeOH).

NTA-(OtBu)3-PEG2000-DTPE (20). Compound 19 (95.5 mg, 0.034 mmol) and compound 13 (205 mg, 0.344 mmol) were dissolved in DCM (5 mL) in a 25 mL round bottom flask with stir bar. The flask was evacuated and flushed with nitrogen. DIEA (60 µL, 0.348 mmol) was added and the solution stirred for 48 hours at ambient temperature under a nitrogen atmosphere. Volatiles were evaporated under reduced pressure and the product was purified by flash chromatography on silica using a gradient of DCM:MeOH as eluent starting with 90:10 moving to 85:15 then finally 80:20. Fractions containing product were pooled, concentrated and dried in vacuo to give compound 20. Yield: 29.0 mg (27%); TLC: $R_f$=0.65 (80:20 DCM:MeOH).

NTA-PEG2000-DTPE (21). Compound 20 (29 mg, 0.009 mmol) and triethylsilane (100 µL, 0.625 mmol) were dissolved in 30% TFA in DCM solution (10 mL) in a 25 mL round bottom flask with stir bar. The solution was stirred under ambient temperature and atmosphere for 1.5 hours. Volatiles were evaporated and the residue was dissolved in 5 mL PBS buffer (pH=7.2) plus 5 mL MeOH. The solution was extracted with CHCl$_3$ (3×8 mL). The organic extracts were dried over anhydrous Na$_2$SO$_4$, filtered, concentrated and dried in vacuo to give compound 21. Yield: 18.0 mg (62%); TLC: $R_f$=0.0 (80:20 DCM:MeOH).

What is claimed is:

1. A method of preparing targets for structural elucidation comprising:
   selectively capturing target proteins by contacting a grid of a thin coating that is modified with a specific capture agent and two deactivating agents with a cell lysate comprising the target proteins; and
   performing structure analysis on the target proteins using a microscopy for structure analysis;
   wherein the coating comprises a graphene oxide sheet, the specific capture agent comprises Nα, Nα-dicarboxymethyllsysine (GO-NTA), and the two deactivating agents are 4-aminobenzoic acid (PABA) and bovine serum albumin (BSA).

2. The method of claim 1, wherein the microscopy is electron microscopy.

3. The method of claim 2, wherein the electron microscopy is a single particle analysis.

4. The method of claim 2, wherein the target proteins are polyhistidine-tagged proteins.

5. The method of claim 1, wherein performing the structure analysis is done at a resolution of between 1 and 10 Angstroms.

6. The method of claim 1, wherein the coating is a monolayer.

7. The method of claim 6, wherein the monolayer is between 0.1 nm and 1 nm thick.

8. The method of claim 1, wherein the cell lysate has been clarified.

* * * * *